United States Patent [19]
Erickson

[11] Patent Number: 5,546,952
[45] Date of Patent: Aug. 20, 1996

[54] METHOD AND APPARATUS FOR DETECTION OF A RESPIRATORY WAVEFORM

[75] Inventor: Donald J. Erickson, Plymouth, Minn.

[73] Assignee: Medtronic, Inc., Minneapolis, Minn.

[21] Appl. No.: 310,362

[22] Filed: Sep. 21, 1994

[51] Int. Cl.$^6$ .................................................. A61B 5/08
[52] U.S. Cl. ............................................................ 128/716
[58] Field of Search ............................... 128/716, 720, 128/721, 722, 723, 724, 725

[56] References Cited

U.S. PATENT DOCUMENTS

| | | |
|---|---|---|
| 4,050,458 | 9/1977 | Friend . |
| 4,074,710 | 2/1978 | Tiep . |
| 4,180,059 | 12/1979 | Tiep . |
| 4,197,856 | 4/1980 | Northrop . |
| 4,248,240 | 2/1981 | van Eykem . |
| 4,296,757 | 10/1981 | Taylor . |
| 4,420,001 | 12/1983 | Hearne . |
| 4,444,201 | 4/1984 | Itoh ................................. 128/716 |
| 4,570,631 | 2/1986 | Durkan . |
| 4,665,926 | 5/1987 | Leuner et al. . |
| 4,696,307 | 9/1987 | Montgleux . |
| 4,781,201 | 1/1988 | Wright et al. . |
| 4,803,997 | 2/1989 | Bowman ............................ 128/716 |
| 4,830,008 | 5/1989 | Meer et al. . |
| 4,834,109 | 5/1989 | Watson . |
| 4,838,279 | 6/1989 | Fore . |
| 4,860,766 | 8/1989 | Sackner . |
| 4,982,738 | 1/1991 | Griebel . |
| 5,050,614 | 9/1991 | Logan . |
| 5,101,831 | 4/1992 | Koyama et al. . |
| 5,105,354 | 4/1992 | Nishimura . |
| 5,133,354 | 7/1992 | Kallok . |
| 5,146,918 | 9/1992 | Kallok et al. . |
| 5,158,080 | 10/1992 | Kallok . |
| 5,167,610 | 12/1992 | Kitado et al. . |
| 5,174,287 | 12/1992 | Kallok et al. . |
| 5,203,343 | 4/1993 | Axe et al. . |
| 5,273,036 | 12/1993 | Kronberg et al. . |
| 5,277,193 | 1/1994 | Takishima et al. . |
| 5,277,194 | 1/1994 | Hosterman et al. ................ 128/721 |
| 5,335,654 | 8/1994 | Rapopon ............................ 128/716 |
| 5,335,657 | 8/1994 | Terry, Jr. et al. . |
| 5,335,666 | 8/1994 | Bowman et al. . |
| 5,385,144 | 1/1995 | Yamanishi et al. ................ 128/716 |

OTHER PUBLICATIONS

"Diaframa–pacing ved elektrisk stimulation af nn. phrenici™ ", Biering–Sorensen, Fin et al. Ugeskr Laeger 152(16):1143–45 1990.

"A Model of Muscular Control of Upper Airway Geometry", Fouke, J. M. et al. J. Biomechanics 23(7):639–646 1989.

"Obstructive Sleep Apnea: Diagnosis and Treatment", Cook, William R. J. et al. South Carolina Med. Assoc. 81(12):647–651 Dec. 1985.

"Diaphragmatic Pacing In Infants: Techniques and Results", Ilbawi, Michel N. et al. Ann. Thorac. Surg. 40(4):323–9 Oct. 1985.

"Diaphragm Pacing: Present Status", Glenn, William W. L. Pace 1:327–370 Jul.–Sep. 1978.

"Effects of Submental Electrical Stimulation during Sleep on Upper Airway Patency in Patients with Obstructive Sleep Apnea", Mikl, Hiroshi et al. Am. Rev. of Resp. Disease 140:1285–89 1989.

(List continued on next page.)

Primary Examiner—Lee S. Cohen
Attorney, Agent, or Firm—Daniel W. Latham; Harold R. Patton

[57] ABSTRACT

A method and device for determining the validity of a respiratory effort waveform from a signal having non-respiratory artifacts includes monitoring a respiratory effort waveform for a parameter of the waveform that is characteristic of a non-respiratory artifact. The parameter is then compared with a predetermined limit to determine whether a valid respiratory waveform has been detected. This is useful for obstructive apnea treatment by electrical stimulation in order to reliably limit electrical stimulation to the inspiratory phase of the respiratory cycle.

20 Claims, 31 Drawing Sheets

OTHER PUBLICATIONS

"Phrenic Nerve Stimulation for Central Ventilatory Failure with Bipolar and Four–Pole Electrode Systems", Baer. Gerhard A. et al. Pace 13(8):1061–72 Aug. 1990.

"A New Treatment for Obstructive Sleep Apnea Syndrome by Electrical Stimulation of Submental Region", Mild, Hiroshi et al. Tohoku J. Exp. Med. 154:91–92 1988.

"Diaphragm Pacing in Infants and Children", Hunt, Carl E. et al. Pace 11(1):2135–2141 1988.

"Pacing the Diaphragm in Infants", Glenn, William W. L. Ann. Thorac. Surg. 40(4):319–20 Oct. 1985.

"Phrenic Nerve Pacing for the Treatment of Central Hypoventilation Syndrome—State of the Art and Case Report", Melsner, H. et al. Thorac. Cardiovasc. Surgeon 31:21–25 1983.

"Phrenic nerve pacing in infants and children: a review of experience and report on the usefulness of phrenic nerve stimulation studies", Brouillette, Robert T. et al. J. Pediatrics 102(1):32–9 Jan. 1983.

"Diaphragm Pacing In Infants and Children: Report of a Simplified Technique and Review of Experience", Ilbawl, Michel N. et al. Ann. Thorac. Surg. 31(1):61–65 Jan. 1981.

"Diaphragm Pacing in Infants and Children: A Life–table Analysis of Implanted Components", Weese–Mayer, Debra E. et al. Am. Rev. Respir. Dis. 139:974–79 1989.

"Congenital central hypoventilation syndrome: A report of successful experience with bllateral diaphragmatic pacing", Coleman, Michael et al. Arch. Disl Child. 55(11):901–3 Nov. 1980.

"Transcutaneous Monitoring as Trigger for Therapy of Hypoxemia During Sleep", Schlaefke, Marianne E. et al. Adv. Exp. Med. Biol (U.S.) 220:95–100 1987.

"Investigations Into Ventilatory Control in Central Alveolar Hypoventilation Syndrome with and without Phrenicus Pacemaker", Grubbauer, H. M. et al. Klin. Padiatr. 200:388–392 1988.

"Electrical Activation of the Diaphragm", Nochomovitz, Michael L. Clinics in Chest Medicine 9(2):349–358 Jun. 1988.

"Physiopathologie des apnees obstructives du sommell", Series, F. et al. Rev. Mal Resp., 397–407 1989.

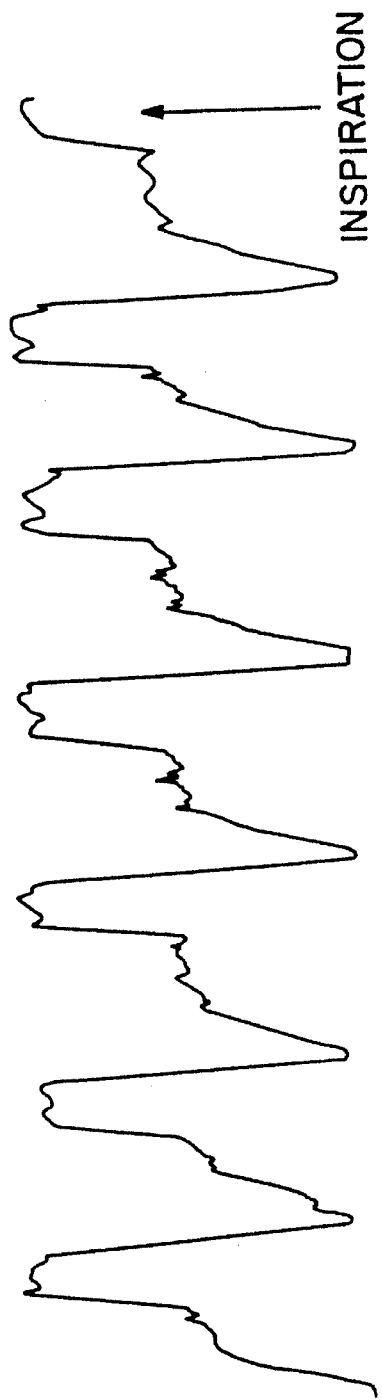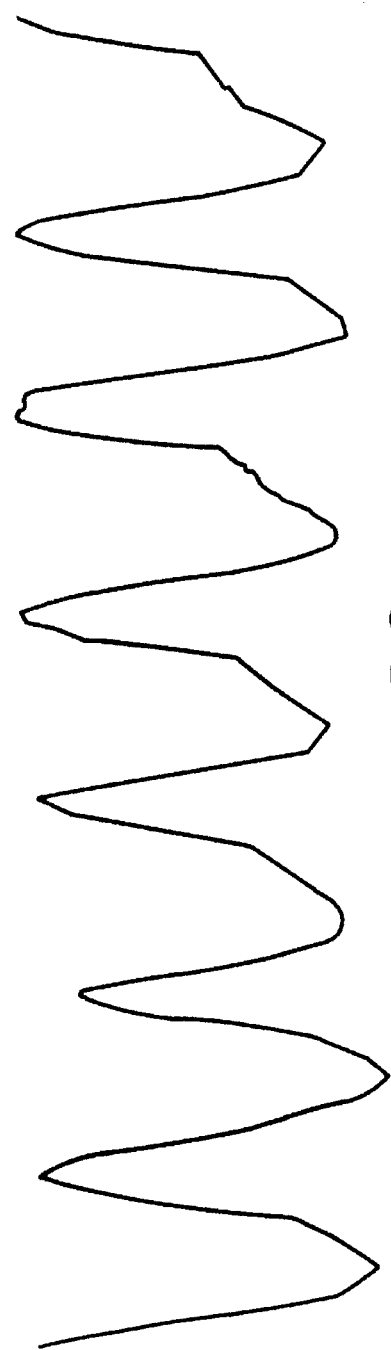

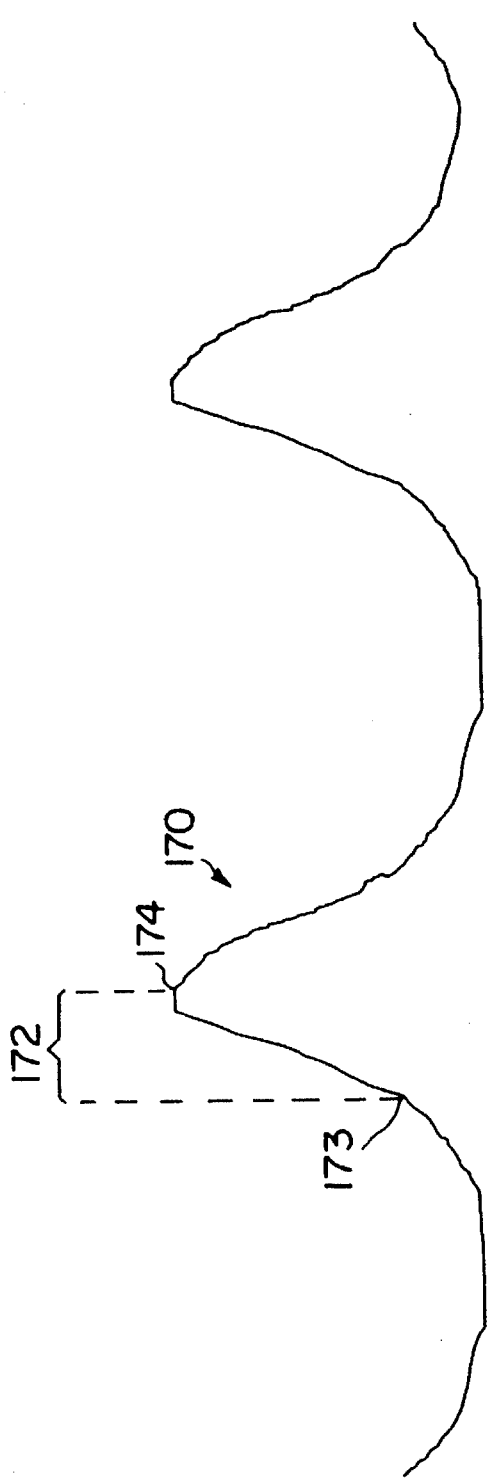
FIG.9a RESPIRATORY SIGNAL
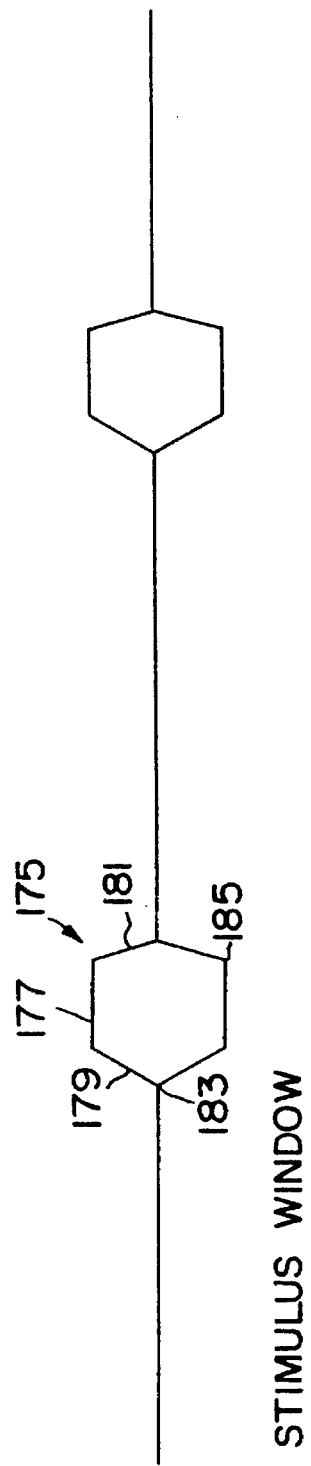
FIG.9b STIMULUS WINDOW

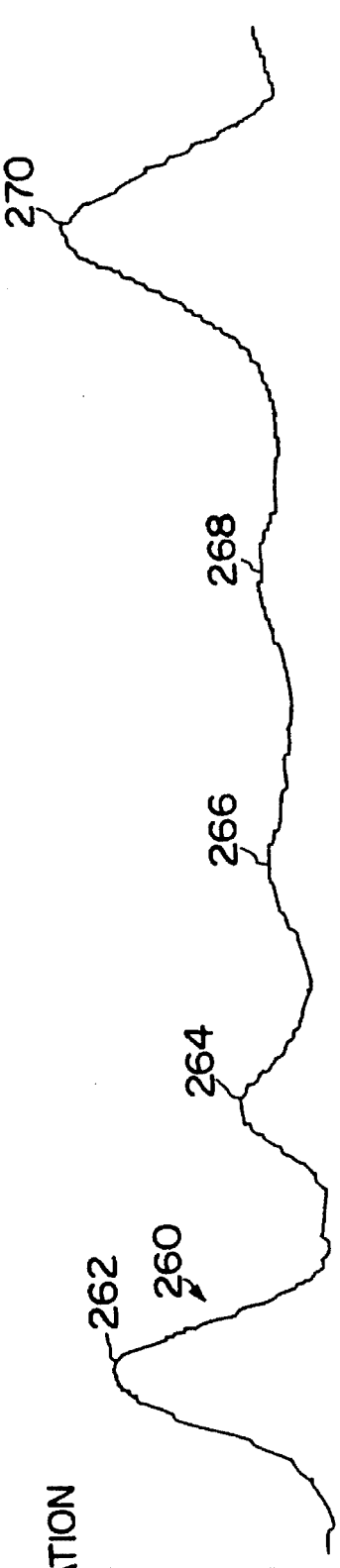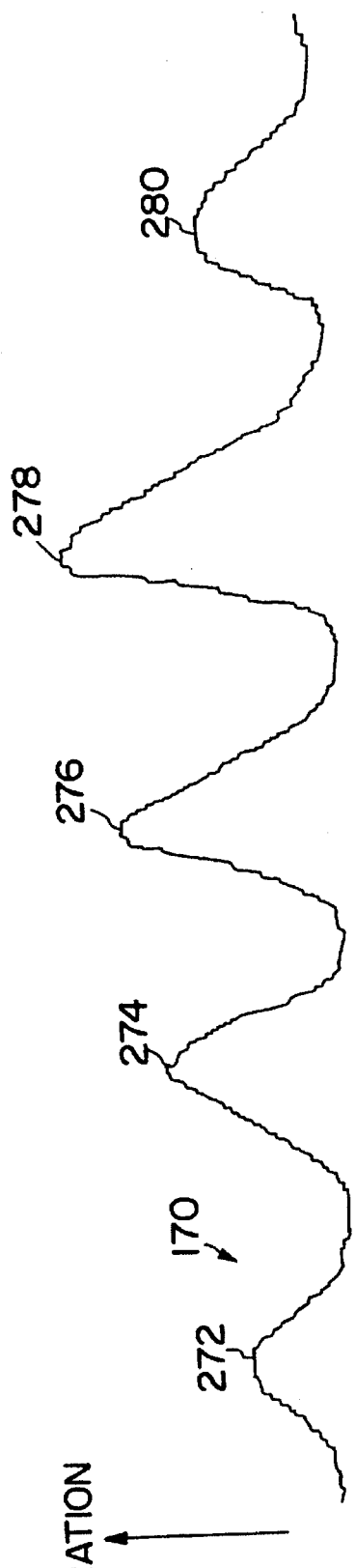

METHOD AND APPARATUS FOR DETECTION OF A RESPIRATORY WAVEFORM

BACKGROUND OF THE INVENTION

The present invention relates to medical devices which employ electrical stimulation in the treatment of sleep apnea.

Sleep apnea has been known for some time as a medical syndrome in two generally recognized forms. The first is central sleep apnea, which is associated with the failure of the body to automatically generate the neuro-muscular stimulation necessary to initiate and control a respiratory cycle at the proper time. Work associated with employing electrical stimulation to treat this condition is discussed in Glenn, "Diaphragm Pacing: Present Status", Pace, V. I, pp 357–370 (July–September 1978).

The second sleep apnea syndrome is known as obstructive sleep apnea. Ordinarily, the contraction of the dilator muscles of the upper airways (nose and pharynx) allows their patency at the time of inspiration. In obstructive sleep apnea, the obstruction of the airways results in a disequilibrium between the forces which tend to their collapse (negative inspiratory transpharyngeal pressure gradient) and those which contribute to their opening (muscle contraction). The mechanisms which underlie the triggering of obstructive apnea include a reduction in the size of the superior airways, an increase in their compliance, and a reduction in the activity of the muscle dilator. The muscle dilators are intimately linked to the respiratory muscles and these muscles respond in a similar manner to a stimulation or a depression of the respiratory center. The ventilatory fluctuations observed during sleep (alternately hyper and hypo ventilation of periodic respiration) thus favors an instability of the superior airways and the occurrence of oropharyngeal obstruction. The respiratory activation of the genioglossus has been particularly noted to be ineffective during sleep. The cardiovascular consequences of apnea include disorders of cardiac rhythm (bradycardia, auriculoventricular block, ventricular extrasystoles) and hemodynamic (pulmonary and systemic hypertension). This results in a stimulatory metabolic and mechanical effect on the autonomic nervous system. The electroencephalographic awakening which precedes the easing of obstruction of the upper airways is responsible for the fragmentation of sleep. The syndrome is therefore associated with an increased morbidity (the consequence of diurnal hypersomnolence and cardiovascular complications).

A method for treatment of obstructive sleep-apnea syndrome is to generate electrical signals to stimulate those nerves which activate the patient's upper airway muscles in order to maintain upper airway patency. For example, in U.S. Pat. No. 4,830,008 to Meer, inspiratory effort is monitored and electrical signals are directed to upper airway muscles in response to the monitored inspiratory effort. Or, in U.S. Pat. No. 5,123,425 a collar contains a sensor to monitor respiratory functioning to detect an apnea episode and an electronics module which generates electrical bursts to electrodes located on the collar. The electrical bursts are transferred transcutaneously from the electrodes to the nerves innervating the upper airway muscles. Or in U.S. Pat. No. 5,174,287 issued to Kallok, sensors monitor the electrical activity associated with contractions of the diaphragm and also the pressure within the thorax and the upper airway. Whenever electrical activity of the diaphragm suggests that an inspiration cycle is in progress and the pressure sensors show an abnormal pressure differential across the airway, the presence of obstructive sleep apnea is assumed and electrical stimulation is applied to the musculature of the upper airway. Or, in U.S. Pat. No. 5,178,156 issued to Wataru et al, respiration sensing includes sensors for sensing breathing through left and right nostrils and through the mouth which identifies an apnea event and thereby triggers electrical stimulation of the genioglossus. Or, in U.S. Pat. No. 5,190,053 issued to Meer, an intra-oral, sublingual electrode is used for the electrical stimulation of the genioglossus to maintain the patency of an upper airway. Or in U.S. Pat. No. 5,211,173 issued to Kallok et at, sensors are used to determine the effectiveness of the stimulation of the upper airway and the amplitude and pulse width of the stimulation are modified in response to the measurements from the sensors. Or in U.S. Pat. No. 5,215,082 issued to Kallok et al, upon sensing of the onset of an apnea event, a stimulation generator provides a signal for stimulating the muscles of the upper airway at a varying intensity such that the intensity is gradually increased during the course of the stimulation. However, even with these modes of therapy there remain many practical difficulties for implementing them in a medically useful treatment system. In particular, if stimulation occurs in response to detected inspiration or to misdetected apnea events, the stimulation may make it difficult for the patient to get to sleep initially or to return to sleep after awakening. According to the Meer '008 patent, the solution to this problem is to monitor the action potentials of the upper airway muscles to determine when the patent is awake and to commence stimulation only when normal upper airway muscle activity is not detected. However, this approach presents many practical difficulties in implementation and can lead to inappropriate stimulation or failure to stimulate reliably.

It is therefore an object of the invention to provide a method for detection of a valid respiratory effort waveform from a signal which includes non-respiratory artifacts such as body movement and cough artifacts.

SUMMARY OF THE INVENTION

A method for determining the validity of a respiratory effort waveform from a signal having non-respiratory artifacts includes monitoring a respiratory effort waveform for a parameter of the waveform that is characteristic of a non-respiratory artifact. The parameter is then compared with a predetermined limit to determine whether a valid respiratory waveform has been detected. This method of waveform detection is based on the observed differences between the slow, regular respiratory effort waveform traces made during normal respiration during sleep and the much more rapid traces made by a cough or body movement. The selected parameter of the waveform can be, for example, inspiratory rise time, inspiratory time-to-peak, time of inspiratory onset to expiratory offset, inspiratory peak-to-peak time, expiratory peak-to-peak time or breath-to-breath time. For example, a rapid rise in the waveform following detection of the start of inspiration is more characteristic of movement of the patient's body than it is of respiration during sleep. One can therefore monitor the inspiratory rise time of the respiratory effort and unless it is more than about 220 milliseconds, it can be concluded that what has been detected is an artifact, not a valid waveform. Further, if the inspiratory rise time is more than a predetermined time, it is possible that the valid respiratory waveform is no longer being tracked by the system. This can be determined by reference to a baseline average for the parameter. For example, if the inspiratory rise time is more than the baseline average plus an amount in the range of about 625 to 950 milliseconds, it is probable that a valid respiratory waveform is no longer being tracked. Limits for other parameters can be similarly established. For example, if the monitored parameter is the inspiratory time-to-peak time, a time of more than 750 milliseconds and less than a baseline average for the parameter plus an amount in the range of about 875 to 1300 milliseconds is indicative of a valid respiratory waveform. Or, if the monitored parameter is the time of inspiratory onset to expiratory offset, a time of more than 1000 milliseconds and less than a baseline average for the parameter plus an amount in the range of about 1125 to 1700 milliseconds is indicative of a valid respiratory waveform. Or, if the monitored parameter is the inspiratory peak-to-peak time or the expiratory peak-to-peak time or the breath-to-breath time (measures of length of a single respiratory cycle), a time of less than 2000 milliseconds and less than a baseline average for the parameter plus an amount in the range of about 2000 to 4000 milliseconds is indicative of a valid respiratory waveform.

If additional evidence of a valid respiratory waveform is desired, multiple parameters can be monitored and compared with their respective limits before a determination as to the validity of the waveform is made. Also, the value of the parameter can be an average value rather than a single data point. For example, two or three values for the parameter can be averaged and compared with the predetermined limit.

Since it is desirable in apnea treatment to limit electrical stimulation of the patient to the inspiratory phase of the respiratory cycle, a valid respiratory effort waveform should be available to synchronize the initiation and termination of stimulation with inspiration. Therefore, when a valid respiratory effort waveform is not detected, electrical stimulation is suppressed.

A medical device which embodies this method of respiratory waveform detection can be made according to the detailed description which follows.

BRIEF DESCRIPTION OF THE DRAWINGS

FIGS. 2a–c are graphs of normal respiratory waveforms (shown with full normal inspiration at the peak). FIG. 2a shows a respiratory effort waveform and indicated phases of the respiratory effort waveform. FIG. 2b shows a graph of a respiratory airflow waveform with FIG. 2c showing the corresponding respiratory effort waveform.

FIGS. 9a and 9b are waveforms showing the synchronization of stimulation from the upper airway transmitter of FIG. 5 (FIG. 9b) with the respiratory waveform (FIG. 9a).

FIG. 21 provides a comparison between the respiratory effort waveform according to FIG. 18 during an apnea event (FIG. 21b) with the waveform for inspiratory airflow (FIG. 21a).

DETAILED DESCRIPTION OF THE PREFERRED EMBODIMENTS

Figure 1:
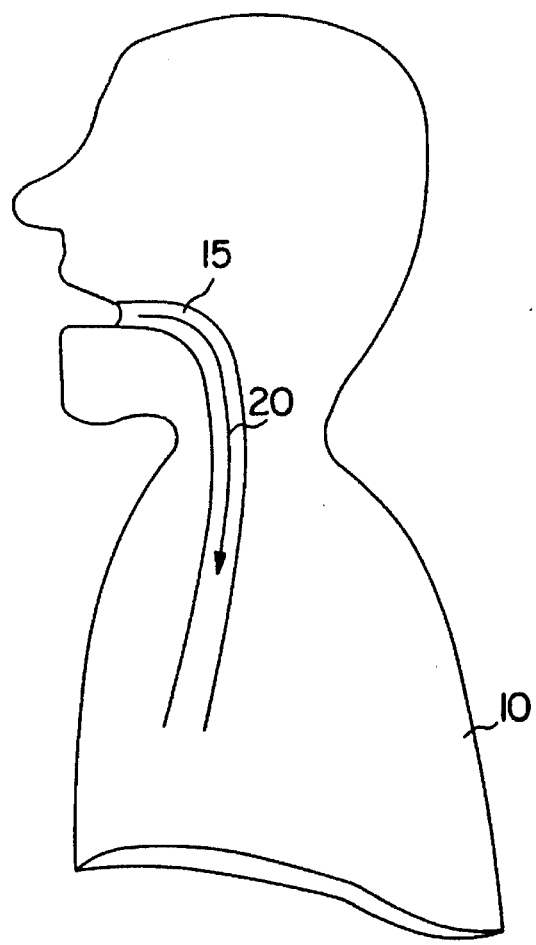
FIG. 1 is a side sectional diagram of a patient having normal respiratory activity.
Figure 2A:
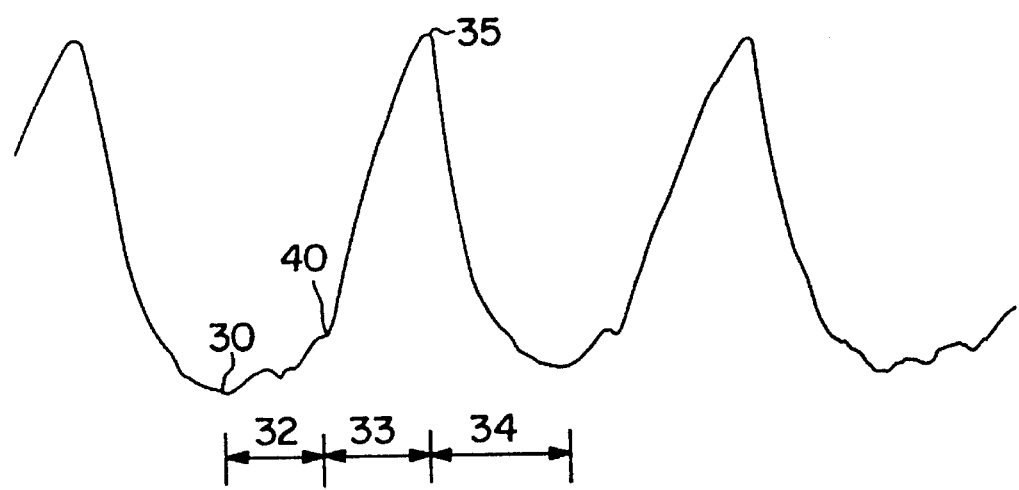

The present invention relates to an apparatus and method for treatment of obstructive apnea by administering stimulation of the musculature of the upper airway in synchrony with the inspiratory phase of the respiratory cycle. In FIGS. 1 and 2a–c, normal respiratory activity is depicted. In FIG. 1, a patient 10 has an airway 15 which is remains patent during inspiration of air 20. FIG. 2a shows a typical respiratory effort waveform for two complete respiratory cycles. This analog waveform can be generated by a belt transducer (e.g. an EPMS Systems Resp-Ez Respiratory Belt Transducer) worn snugly about the chest of the patient. This is a conventional type of belt transducer that is used for detection and analysis of sleep apneas in sleep laboratories. Each wave of the waveform is characterized by a negative peak 30 on completion of expiration, a positive peak 35 on completion of inspiration and a turning point 40 which indicates the onset of inspiration. Each wave of the waveform can therefore be separated into a period of respiratory pause 32, an inspiratory phase 33 and an expiratory phase 34. Respiratory effort waveforms having the same identifiable characteristics can be provided by monitoring other physiological signals such as intrathoracic pressure, intrathoracic impedance or electromeyographic potentials. Other characteristics of the waveform could also be identified in connection with tracking and analyzing the respiratory waveform to monitor respiratory activity in sleep apnea treatment. In normal respiration, the respiratory effort waveform is related to airflow as set forth in FIGS. 2b and 2c. In FIG. 2b a trace of normal respiratory airflow from a flow transducer is shown while FIG. 2c shows the corresponding trace of the normal respiratory effort which produces the airflow.

Figure 3:
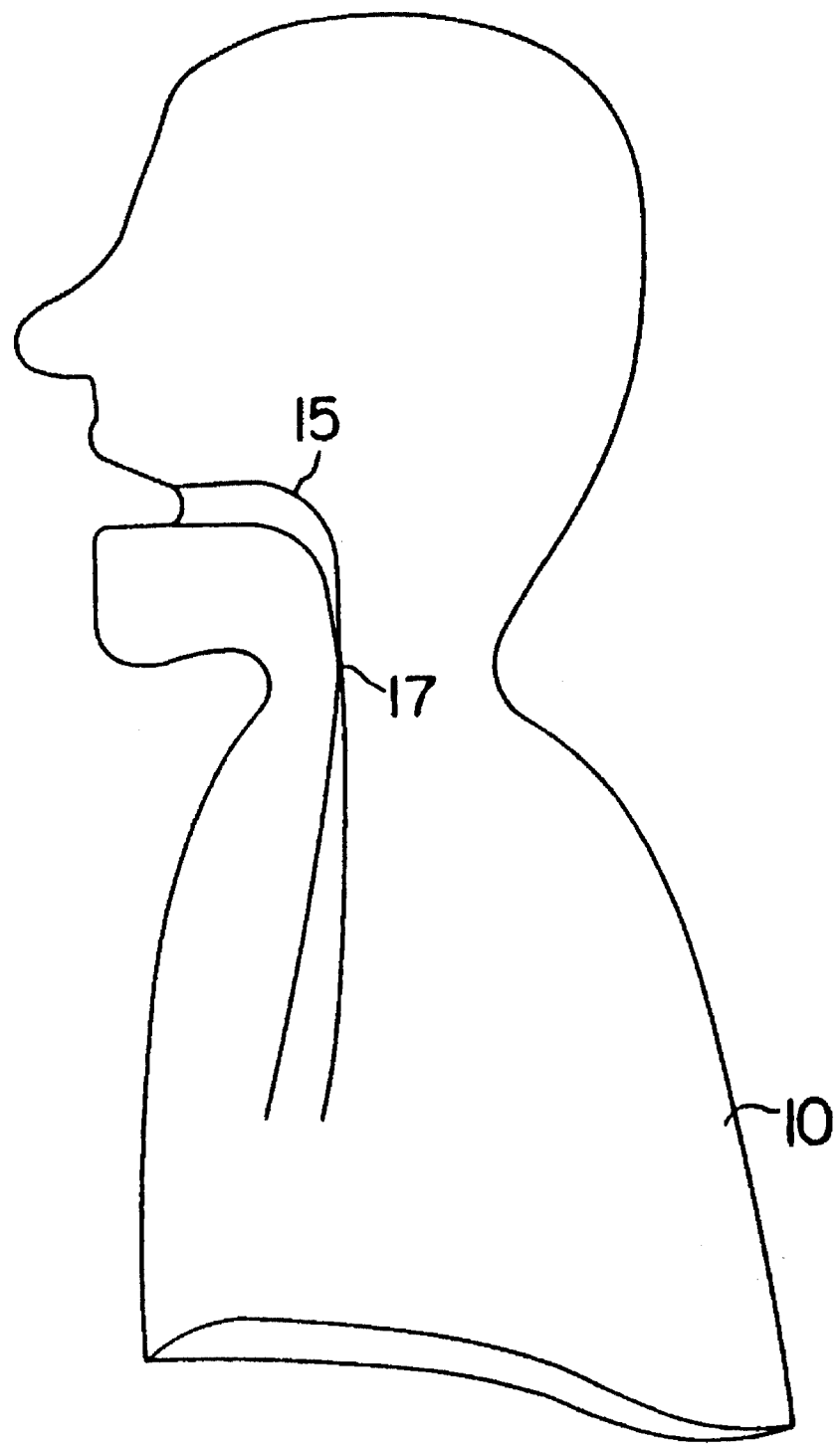
FIG. 3 is a side sectional diagram of the patient of FIG. 1 at the onset of to obstructive apnea.
Figure 4A:
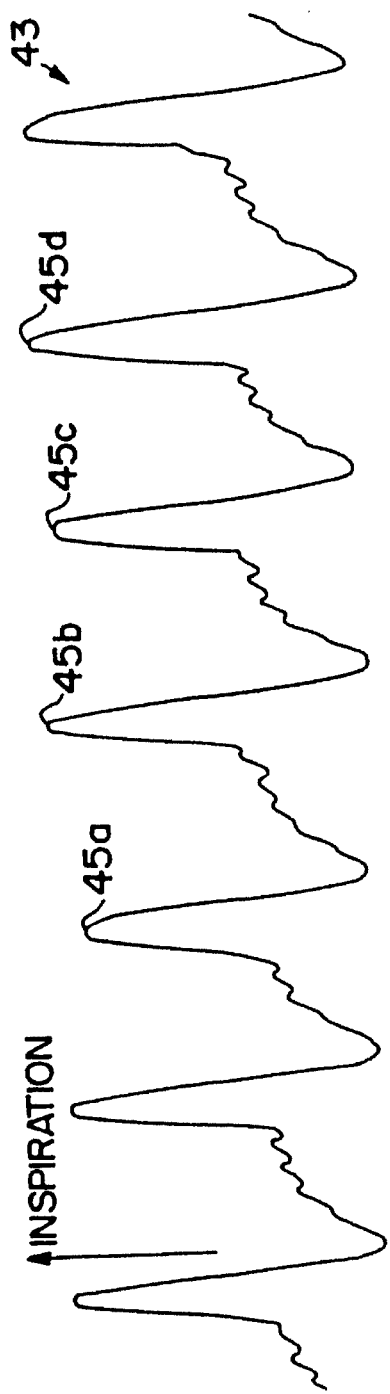
FIGS. 4a and 4b are respiratory waveforms of inspiratory effort showing normal inspiratory effort (FIG. 4a) and the change in normal inspiratory effort at the onset of an apnea event (FIG. 4b).
Figure 4B:
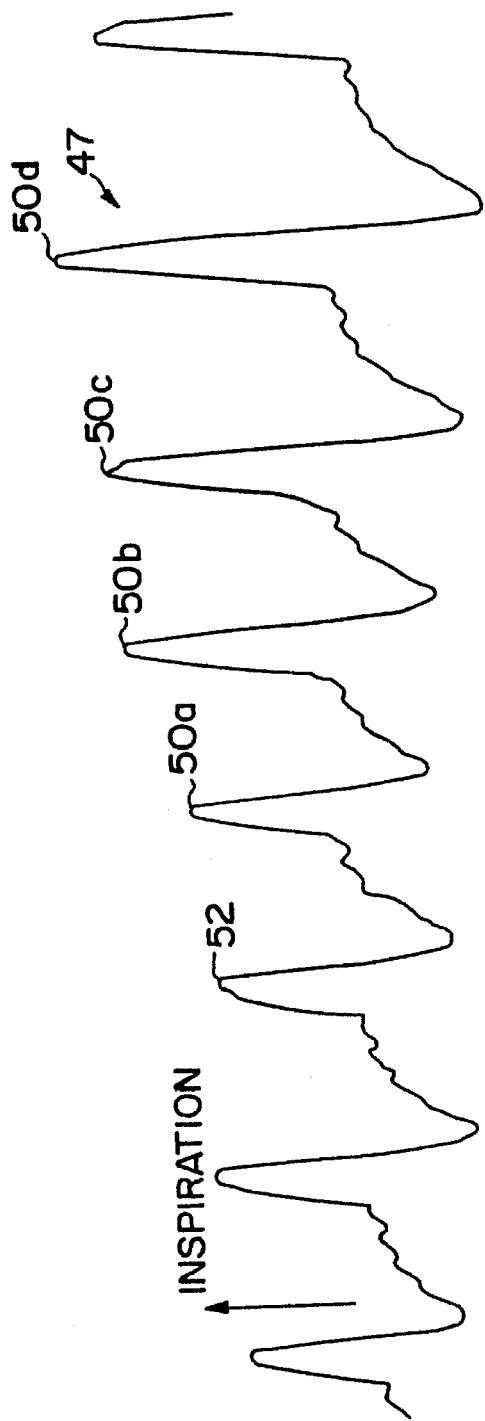

In FIGS. 3 and 4b, respiration in the same patient at the onset of an obstructive sleep apnea event is depicted. FIG. 3 shows the patient 10 and airway 15 with an airway obstruction 17 that is characteristic of an obstructive apnea event. FIG. 4a shows that in a normal respiratory effort waveform 43, the inspiratory peaks 45a–d are of approximately the same amplitude. By comparison in FIG. 4b, in a waveform 47 the inspiratory peaks 50a–d become significantly greater in amplitude at the onset of obstructive apnea than the immediately preceding inspiratory peak 52. This is reflective of the increased inspiratory effort undertaken by the patient in response to the difficulty of breathing through the obstructed airway.

Figure 4C:
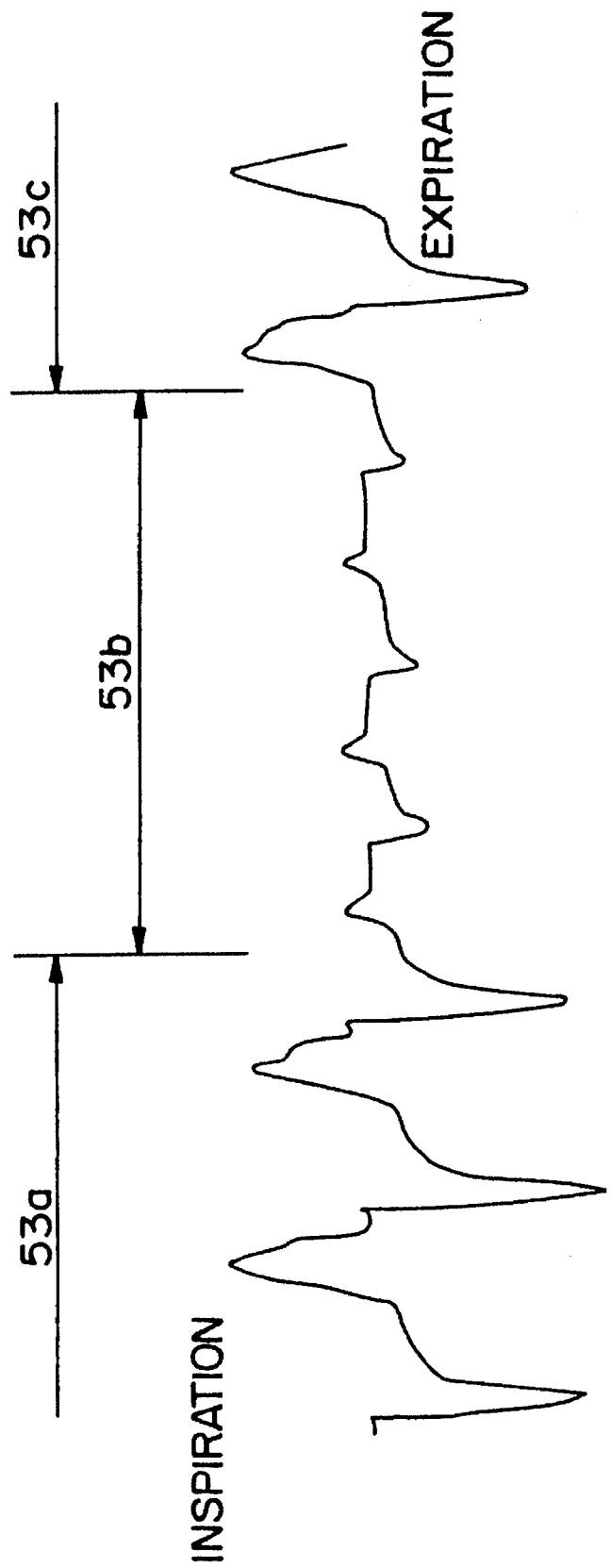
FIG. 4c is a respiratory waveform showing respiratory airflow (as opposed to the respiratory effort waveform shown in FIGS. 4a and 4b) in a patient during an apnea event.
Figure 5:
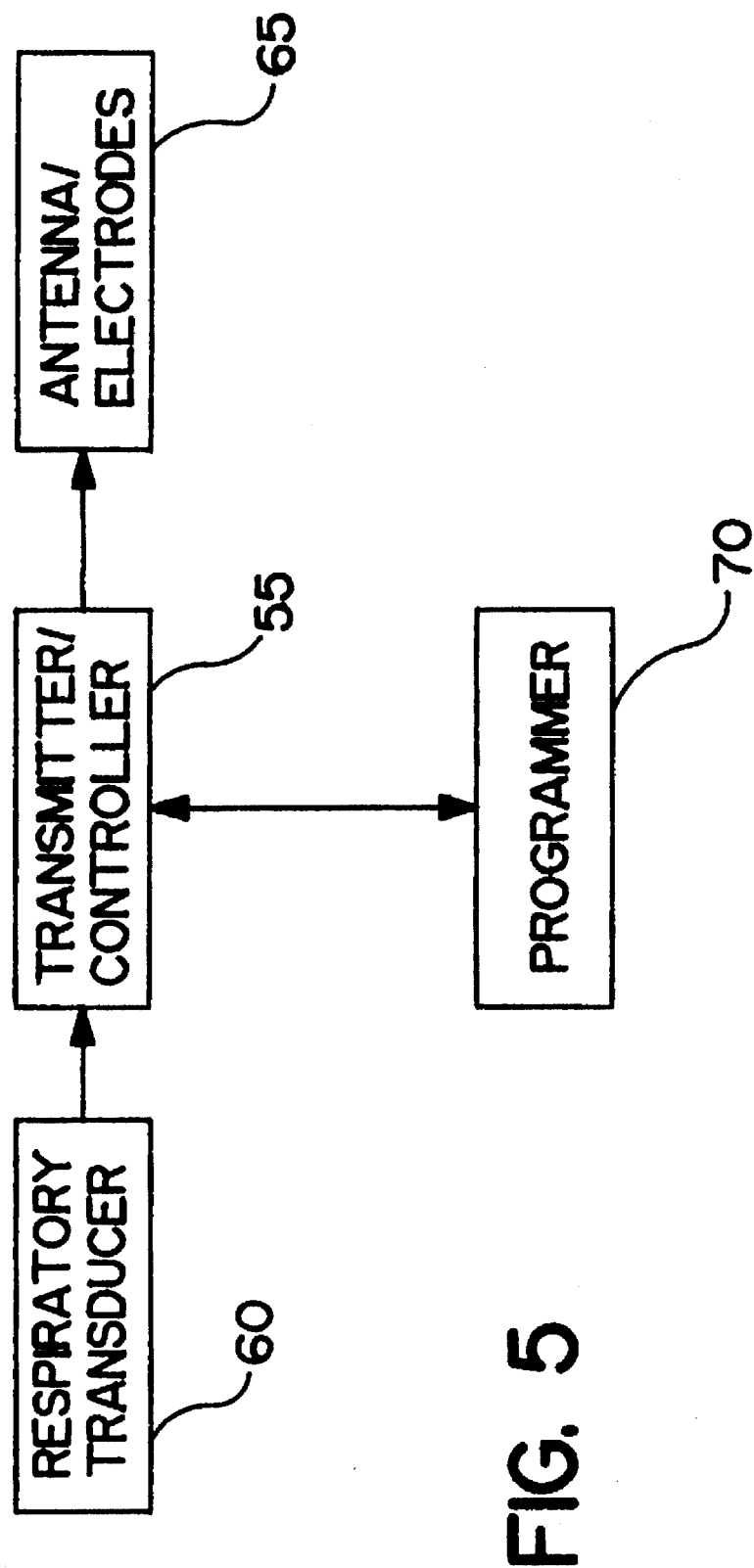
FIG. 5 is a block diagram of one embodiment of the apnea treatment device according to the present invention.

In the device and method of the present invention, the increased respiratory effort is avoided by synchronized stimulation of a muscle in the upper airway which hold the airway open during the inspiratory phase. Preferably, the muscle stimulated is the genioglossus muscle stimulated by a cuff electrode placed around the hypoglossal nerve. The effect of this stimulation on obstructive sleep apnea can be seen in the airflow trace of FIG. 4c. During a first period indicated as 53a, stimulation is enabled producing a normal respiratory airflow. During a second period indicated as 53b, stimulation is disabled causing obstruction of the airway and reduction in airflow volume (apnea). During a third period indicated as 53c, stimulation is resumed, restoring patency to the airway and increasing airflow volume. A block diagram of the principal elements of a device which can accomplish this is shown in FIG. 5. That device includes a transmitter/controller 55 which is capable of sensing the inspiratory phase and transmitting an electrical stimulus pulse to muscles of the upper airway. The transmitter/controller 55 could be either an implantable or an external device but the following description will relate primarily to a battery powered external device. A respiratory transducer 60 such as a conventional belt transducer sends respiratory waveform information to the transmitter/controller 55 which sends stimulus pulses through an antenna/electrode system 65 to stimulate the muscles of the patient. The antenna/electrode system can be a conventional system for bipolar RF coupled muscle stimulation (e.g. a Medtronic model 3538A RF Antenna coupled to a Medtronic Model 3642B Bipolar Receiver and Medtronic Model 3990 Half Cuff Nerve Electrode). As described therein, a surgically implanted receiving antenna, lead and electrode are radio frequency coupled transcutaneously to an external transmitting antenna that is attached to the transmitter/controller. A highly desirable addition to such a system is that of a programmer 70 (such as a laptop PC with serial communication software) which is capable of programming the transmitter/controller 55 with various parameters in order to adapt the device to a particular patient. The device of FIG. 5 is therefore adapted to be programmed by the doctor and thereafter used each night by the patient to prevent the closure of the upper airway during the inspiratory phase of the respiration cycle. It will be apparent to those skilled in the art that such a device must be made to be easy to use by the patient and since it is used without constant medical supervision, it must be able to safely adapt to many different operating conditions.

Figure 6:
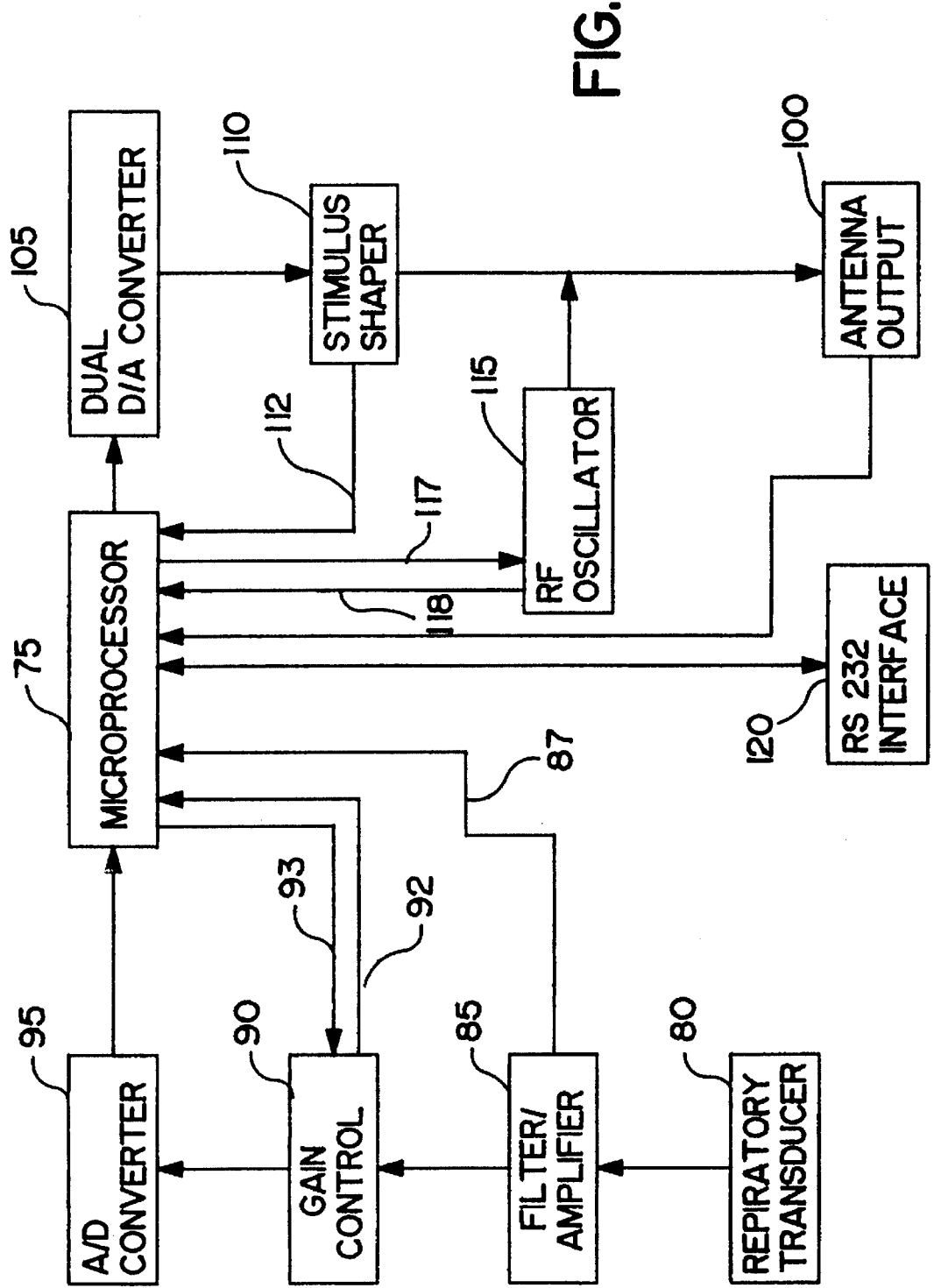
FIG. 6 is a block diagram of the upper airway transmitter/controller of FIG. 5.

FIG. 6 is a block diagram of the transmitter/controller 55 of FIG. 5. A microprocessor 75 (Motorola 68HC05B6) controls the principal operations of the transmitter/controller 55. A respiratory transducer 80 on a respiratory belt (EPMS Systems Resp-Ez Respiratory Belt Transducer) produces a raw differential respiratory waveform signal from about ±10 to ±100 millivolts. The signal is typically the electrical output of the terminals of a piezoelectric crystal mounted on the respiratory belt. The signal from the transducer 80 is coupled to filter/amplifier circuitry 85 which filters, amplifies the differential signal so that it is compatible with an analog/digital converter 95. An output 87 to the microprocessor 75 indicates whether the respiratory transducer 80 is connected to the transmitter/controller 55. This allows the microprocessor 75 to produce an error indication and/or shut down the stimulus from the device when the respiratory transducer 80 is not connected. A gain control 90 is coupled to the circuitry providing the respiratory offset signal 85. The gain control 90 includes an output 92 to the microprocessor 75 and an input 93 from the microprocessor 75 which sets the signal at a proper level for use by the analog/digital converter 95. The analog/digital converter 95 is coupled to the gain control 90 and to the microprocessor 75. The analog/digital converter 95 produces a digital output to the microprocessor 75 in the range from 0–255 depending on the input voltage (a monopolar voltage in the range of 0–2.5 volts). The gain control 90 adjusts the voltage to provide an average digital output in about the middle of the 0–255 range and an offset range (measured from positive peak to negative peak of the waveform) covering about 80% of the 0–255 range. Sampling of the offset signal occurs about every 31 milliseconds as established by the clock rate for the system. This produces a digitized respiratory waveform with enough definition to be readily analyzed for respiratory phases by the microprocessor 75.

The microprocessor 75 identifies the inspiration phase of the waveform so that the system can supply a shaped stimulus burst for the duration of that phase at the antenna output 100. The microprocessor 75 is coupled to a dual digital/analog converter 105 which is also coupled at its output to analog circuitry which acts as a stimulus shaper 110. These elements work in combination to provide a shaped "stimulus window" which controls when stimulation will be provided and how much stimulation will be provided at the antenna output 100. The RF coupled stimulus burst is provided within this window. The microprocessor 75 sets the digital values for the digital/analog converter 105. The dual digital/analog converter 105 is connected in a cascaded arrangement with a first digital/analog section setting the amplitude of the stimulus pulse (i.e. from 0 to 8 volts in 256 increments of 32 millivolts) and the second digital/analog section setting the shape of the stimulus burst (i.e. the shape and duration of the stimulus during a rise time interval and a fall time interval as functions having 0–100% of full amplitude with eight bit resolution ($1/256$) for each 31 millisecond interval of output—typically, a linear ramping function of 250 millisecond for rise time and a linear ramping function of 125 millisecond for fall time is the default setting, or, to turn the stimulus on more quickly, a nonlinear ramping function, such as a sine function, could be used). An input 112 to the microprocessor 75 allows the microprocessor 75 to determine whether the stimulus gain is properly controlled. An RF oscillator 115 supplies a 460 KHz square wave signal which is gated by the microprocessor 75 to a sinusoidal wave with pre-programmed pulse rate and pulse duration (e.g. a rate in the range of 20–50 pulses/second; and a duration of 60–100 microseconds) and is combined with the stimulus window signal from the stimulus shaper 110 to provide the shaped stimulus burst at the antenna output 100. The maximum oscillator output is a peak-to-valley output of 8.0 volts. The oscillator is turned on by the output 117 from the microprocessor 75 which synchronizes the oscillator output with the beginning and end of the stimulus window. Input 119 to a microprocessor timer interrupt controls the timing of the stimulus pulses produces by the oscillator 115.

An RS-232 serial interface 120 allows programmable parameters of the system to be adjusted to conform to the needs of the patient through a standard computer interface. For example, the stimulus pulse amplitude, stimulus pulse duration, stimulus pulse frequency, stimulus burst duration, and stimulus ramp on/off times can be adjusted through the interface 120. In addition, the interface 120 can be used to store and retrieve various data in the system. For example, the patient's name, the code number of the hospital or clinic, the prescription date and the last follow-up date could be stored in the EEPROM of the microprocessor and read out as needed through the serial interface 120. Further, patient compliance data and system performance data could be accumulated by the system and read out through the interface 120. For example, the total time the power is on, the number of power cycles or reset cycles, the average battery voltage and fault detection could be stored in the microprocessor 75 and retrieved through the interface 120 as needed.

Figure 7:
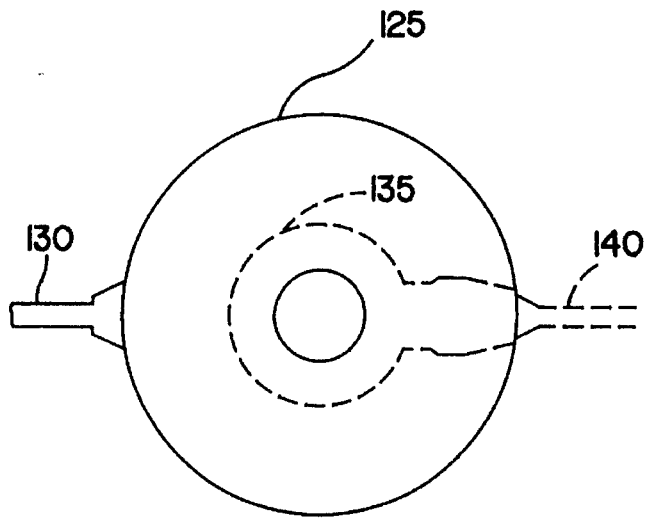
FIG. 7 is a top plan view of the RF output antenna of FIG. 6 coupled to an implanted receiving antenna.

FIG. 7 shows an RF output antenna 125 and lead 130 which would be connected to the transmitter/controller 55 and an implanted receiving antenna 135 and lead 140 in proper alignment for RF coupling with the output antenna 125.

Figure 8:
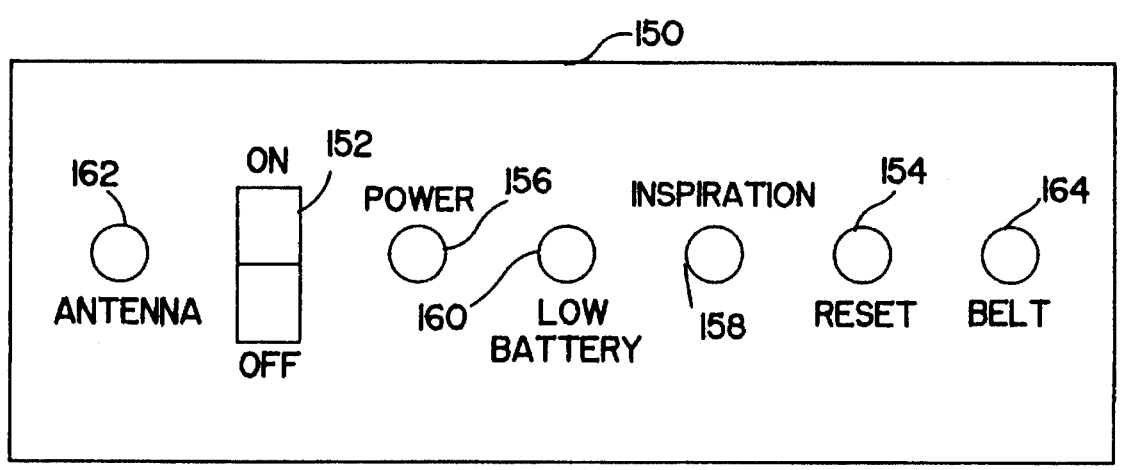
FIG. 8 is a diagram of the control panel for the upper airway transmitter of FIG. 6.

FIG. 8 shows the control panel 150 for the transmitter/controller 55. The control panel 150 includes an on/off switch 152 which allows the patient to turn the stimulation on or off. Turning switch 152 on also automatically resets and reinitializes the system. A momentary reset button 154 allows the patient to recycle the software initialization. For example, the patient would depress the reset button for at least five seconds after arousal to indicate that the stimulus should be halted for a short period until the patient is again asleep. A power-on LED indicator 156 indicates to the patient that the transmitter/controller 55 is on while an inspiration LED indicator 158 is illuminated during the inspiration phase to indicate to the patient that the inspiration phase is being correctly detected. If desired, the power-on LED indicator 156 and inspiration LED indicator 158 could be combined with the combined indicator illuminated during the first five minutes to indicate that the device is on and thereafter illuminated only upon detection of inspiration. The low battery LED indicator 160 provides the patient with an indication that the batteries require changing well in advance of their depletion. (The device uses three AA alkaline batteries in series and a separate long-life lithium backup battery to retain the system clock operation and the programmed parameters in the system while the batteries are being changed or when the system is turned off.) For example, if the system is designed to provide an orderly shut down when the battery voltage drops below 3.2 volts, the indicator 160 can be made to turn on when the voltage drops below 3.6 volts. This indication would allow the patient to replace the batteries and avoid the resumption of obstructive apnea that may occur if the device were to shut down while the patient was asleep. The antenna LED indicator 162 lights in response to a detected disconnect of the RF output antenna 125 from the transmitter/controller 55. The belt LED indicator 164 lights in response to a detected disconnect of the respiratory transducer 60.

FIGS. 9a and 9b indicate the basic mode of operation for the system. The patient's respiratory signal 170 is monitored and the inspiratory phase 172 of the signal 170 is identified from a waveform analysis which finds the turning point 173 and the inspiratory peak 174. The system then provides a bipolar stimulus burst to the appropriate upper airway musculature which is synchronized with the inspiratory phase 172. The shape of the stimulus burst is indicated as a stimulus window 175 which includes a peak amplitude 177 which is specifically set by the physician at a level required by the patient, a ramp 179 gradually increasing the stimulus during a rise time and a ramp 181 gradually decreasing stimulus during a fall time. The peak amplitude 177 is monitored by the microprocessor 75 once per second to determine whether it is within 10% of the prescribed value. Ideally, the stimulus would have a starting point 183 at the same time as the turning point 173 and continue to an end point 185 that is exactly at the inspiratory peak 174. However, due to the fact that there is always uncertainty as to whether the inspiratory peak 174 has been reached or whether the amplitude of the signal will continue to increase, the end point 185 for the stimulus window 175 does not occur until the system clearly identifies the peak by seeing that the signal 170 is on a downward trend. Thus, the end point 185 occurs slightly after the inspiratory peak 174.

Figure 10:
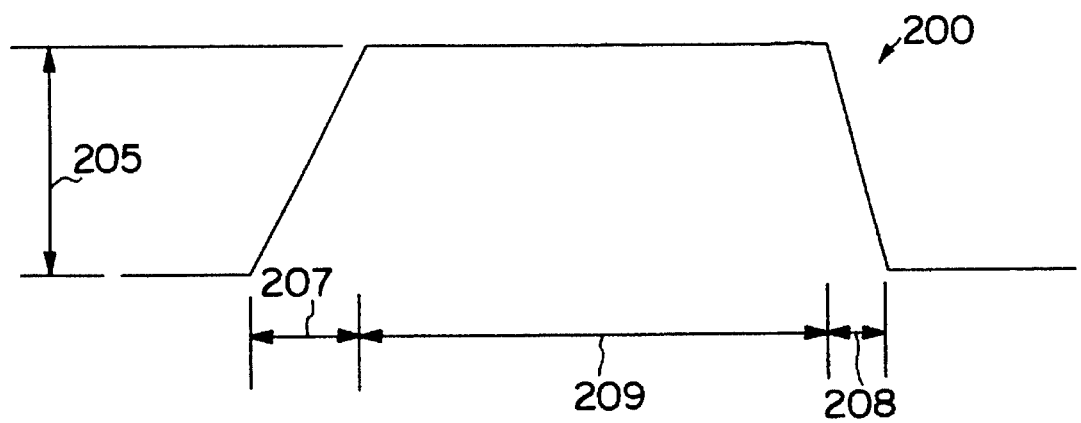
FIG. 10 is a waveform showing the shaping provided by the microprocessor, D/A converter and stimulus shaper of FIG. 6 to make the stimulus burst window of FIG. 9b.
Figure 11:
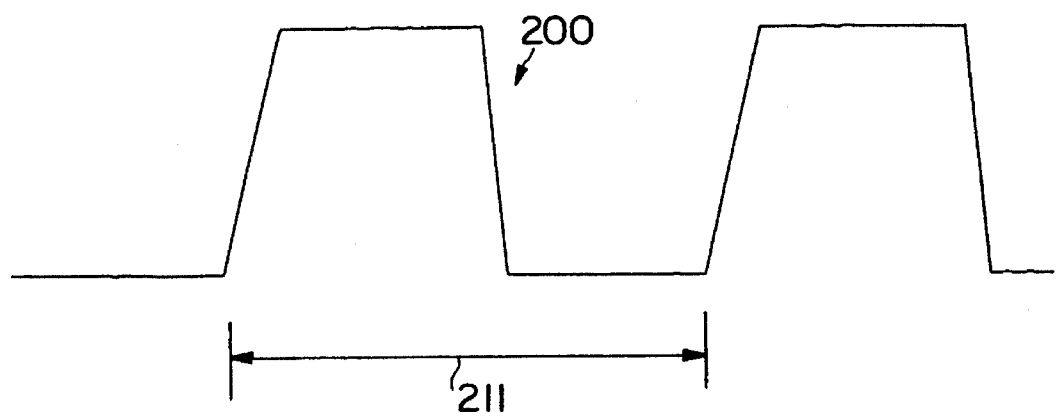
FIG. 11 is a waveform showing two stimulus burst windows as in FIG. 10 and the burst interval.
Figure 12:
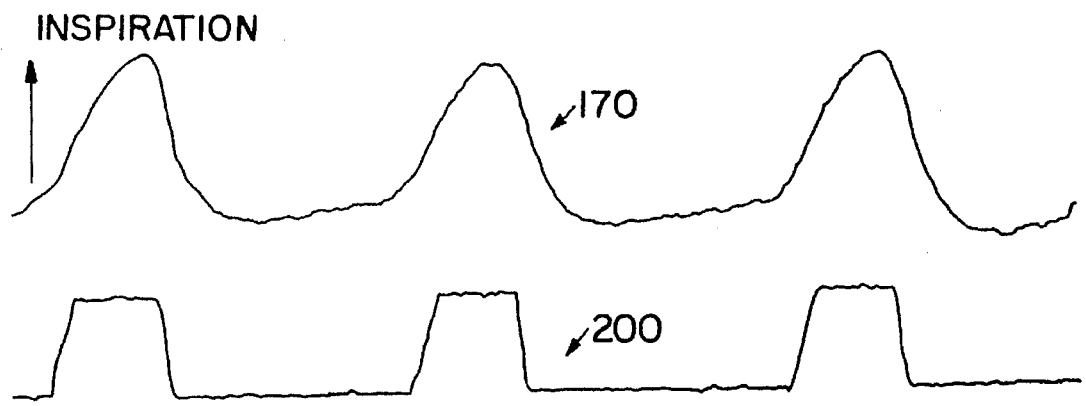
FIG. 12 is a waveform according to FIG. 11 synchronized to the respiratory waveform.
Figure 13:
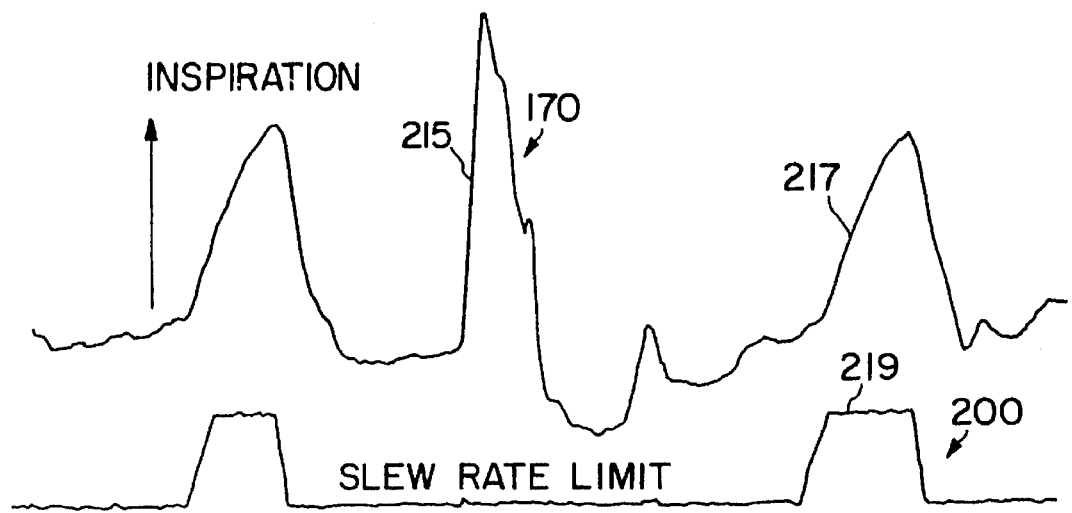
FIG. 13 is a waveform according to FIG. 12 indicating the cessation of stimulation in the presence of a cough or movement artifact.
Figure 14:
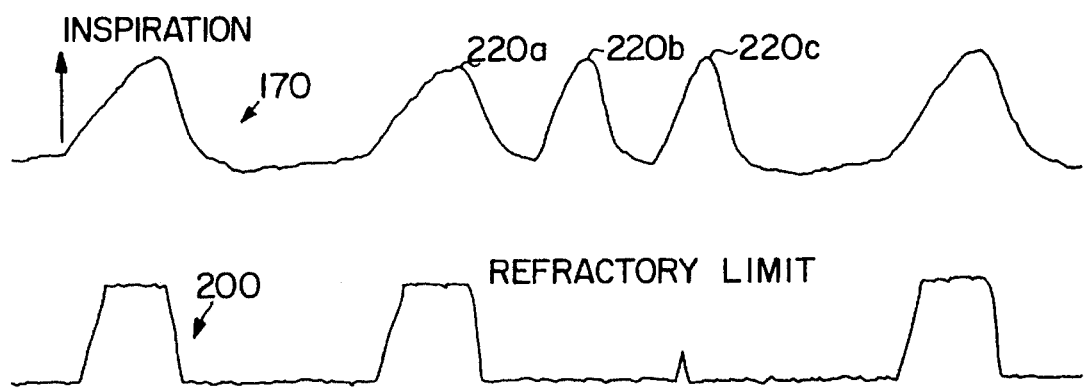
FIG. 14 is a waveform according to FIG. 12 indicating the cessation of stimulus due to the presence of "artifactual" inspiratory signals outside the ordinary refractory period of the respiratory waveform.
Figure 15:
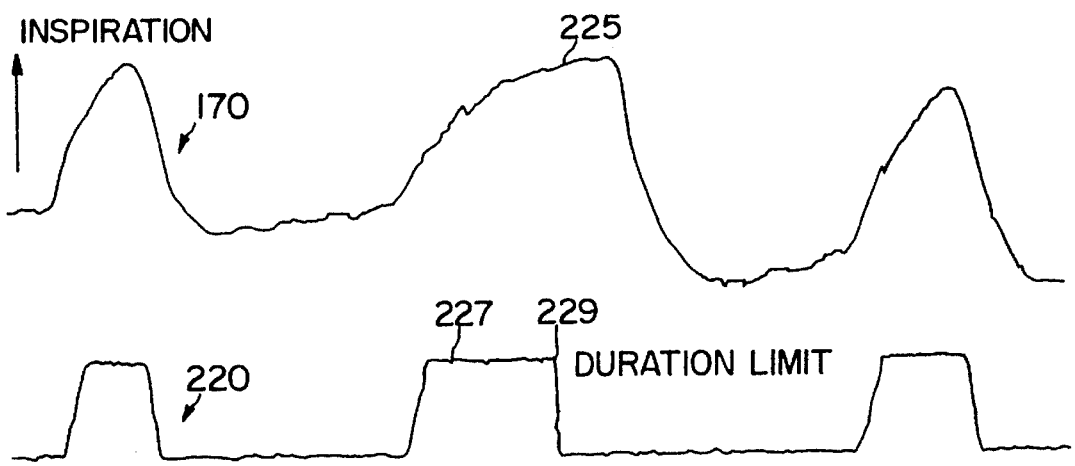
FIG. 15 is a waveform according to FIG. 12 indicating the truncation of the stimulus burst in response to a persistent inspiratory signal in the respiratory waveform.
Figure 16:
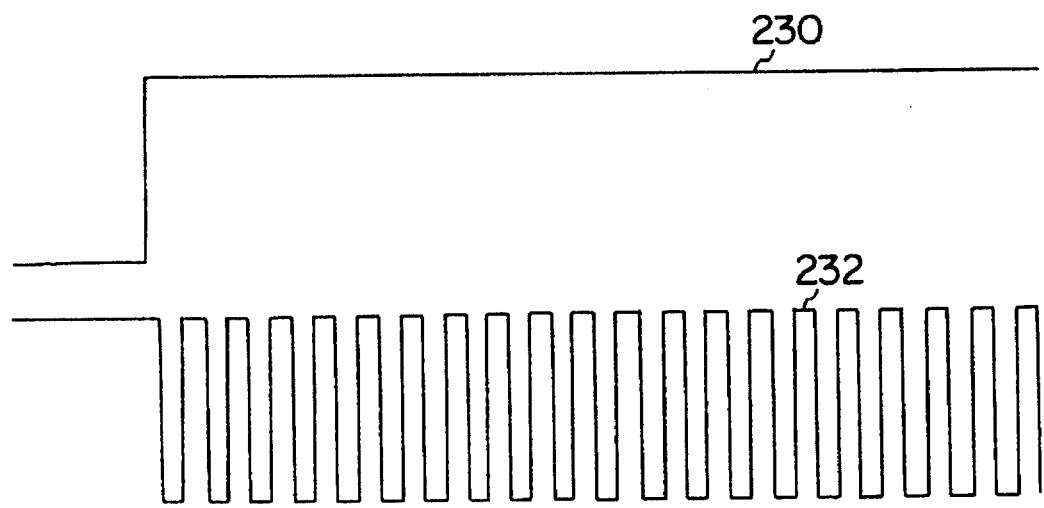
FIG. 16 is a waveform showing the oscillator signal to be combined with each stimulus burst of FIGS. 10–15, the oscillator turned on in response to a signal from the microprocessor.
Figure 17:
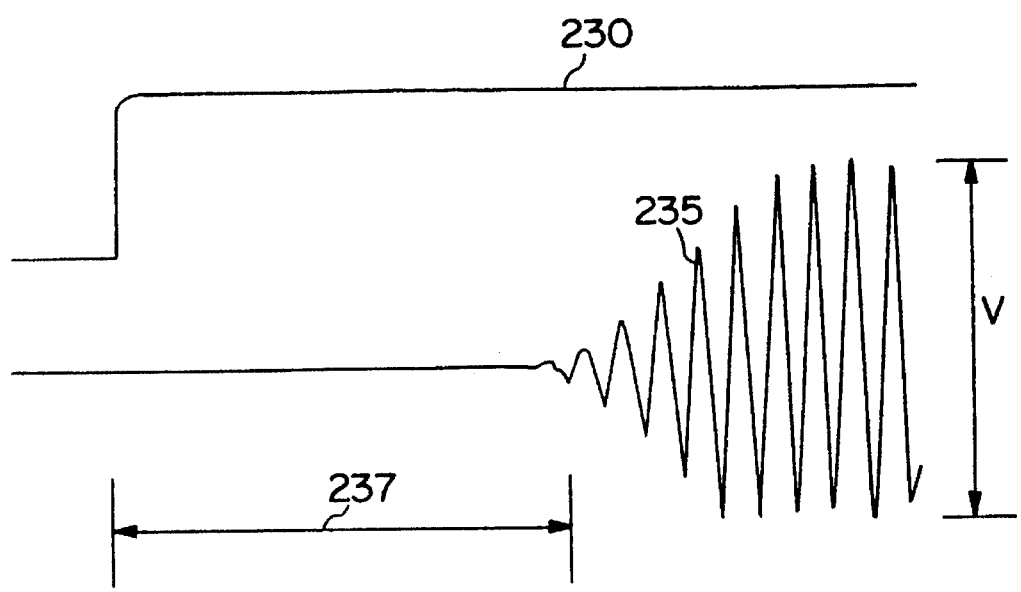
FIG. 17 is an output waveform for the device of FIG. 6 taken at the antenna output showing the shaped stimulus burst window of FIG. 10 with combined oscillator signal of FIG. 16 and RF carrier delay.

FIGS. 10–17 show details of how the stimulus window 175 is formed and is synchronized to the inspiratory phase 172 of the signal 170. FIG. 10 shows a monophasic waveform window 200 shaped with a desired amplitude voltage 205, a stimulus risetime 207, a stimulus falltime 208 and a stimulus plateau 209. The length of time for which the stimulus plateau 209 is maintained is determined by the duration of the inspiratory phase 172 of the signal 170. In FIG. 11, there is a burst interval 211 between the starting point of successive stimulation bursts that is determined as shown in FIG. 12 by the interval between sensed inspiration from the respiratory signal 170. As shown in FIGS. 13–15, there are occasional waveform abnormalities caused by coughs or body movements which should not be allowed to trigger a stimulus or cause a stimulus to be continued for a prolonged period. For example, in FIG. 13, the presence of a rapid rise 215 in the respiratory signal 170 does not trigger a stimulus burst because a slew rate limit has been placed on the method used for inspiration detection. In that instance, the rate at which the slope of the respiratory signal 170 changed was compared with the slew rate limit and found to be beyond the acceptable range for a detected inspiration. A subsequent rise 217 in the respiratory signal 170 is correctly identified as an inspiration and a stimulus pulse 219 is produced in response. In FIG. 14 the presence of three rapid, upward deflections 220a, 220b and 220c in the respiratory signal 170 in close succession does not trigger a stimulus burst for the second 220b or third 220c deflections since a refractory limit established by the normal breathing period of the patient has not been met for the second 220b and third 220c deflections. In FIG. 15, an upward deflection 225 in the respiratory signal 170 continues for an unusually long period of time. Although the stimulus burst 227 is produced in response to this deflection 225, it is terminated at point 229 after a predetermined period of time. FIGS. 16 and 17 show how the RF oscillator provides an RF burst that is synchronous with a stimulus pulse. FIG. 16 shows a control signal (stimulus pulse) 230 which activates the RF oscillator to produce an RF square wave signal 232. This signal 232 is then gated by the stimulus pulse and combined with the monophasic shaping waveform window 200 to form the actual stimulus burst. Wave 235 represents the actual gated RF carrier as measured at the RF antenna which is delayed by an RF carrier delay period 237 of about 20–30 milliseconds.

Figure 18:
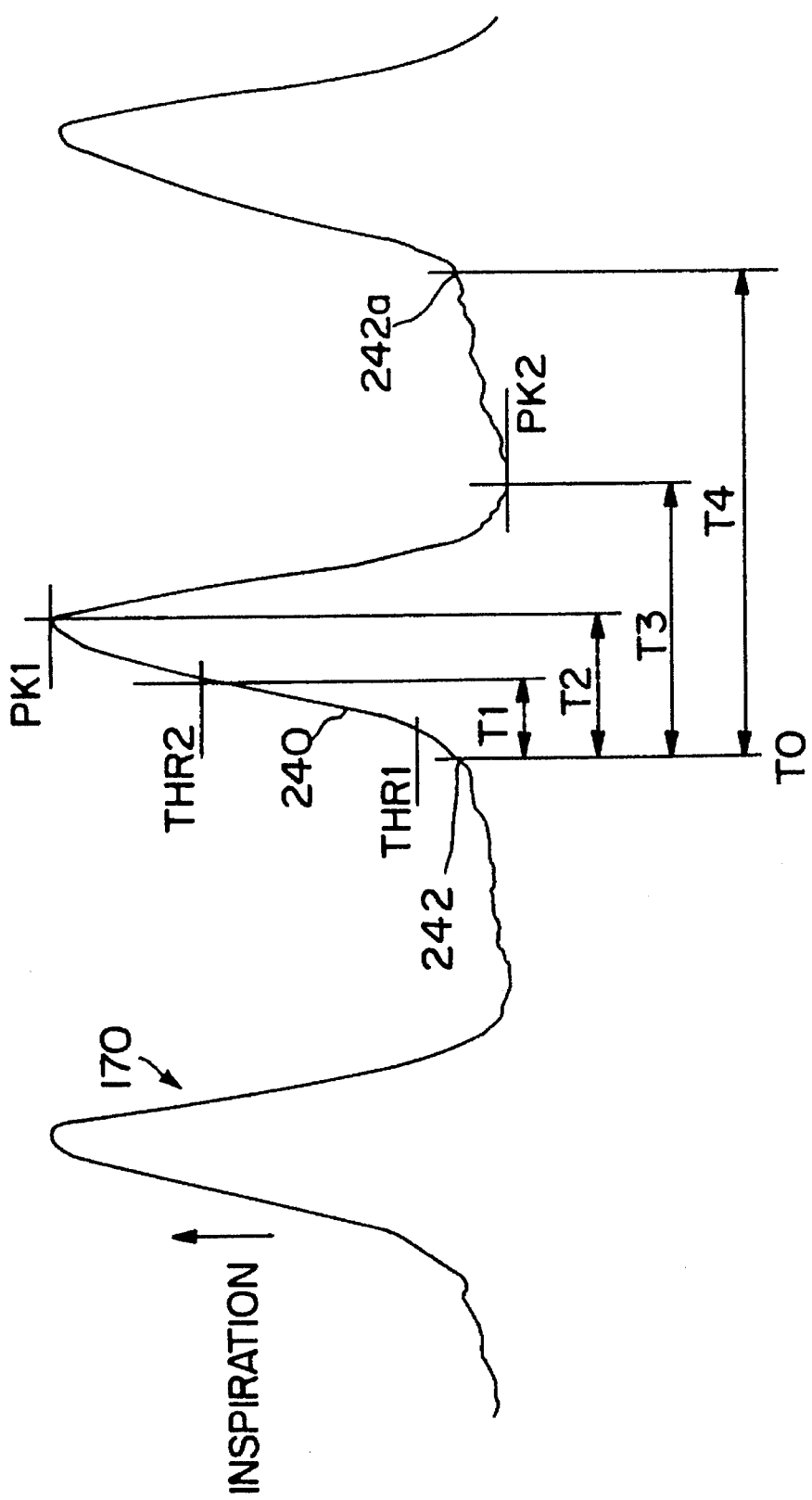
FIG. 18 is a respiratory waveform acquired by the respiratory transducer of FIG. 6 with indicated analysis points for an inspiratory cycle.

Many of the functions of the apnea treatment system are controlled by the microprocessor 75. One of the most important of the microprocessor's functions is to analyze the respiratory signal 170 to determine when stimulation should take place and when it should not. Artifact free respiration is typically a periodic signal like the respiratory signal 170 of FIG. 18. In FIG. 18, inspiration is represented as an upward deflection 240. Each cycle of the respiratory signal 170 can be broken down into three phases. The first is the active inspiratory phase T2 which is the time from the turn point 242 where inspiration begins to the peak PK1 where expiration begins. The second phase is the active expiratory phase from the end of T2 to the end of T3 which is the time from the positive inspiratory peak PK1 to the negative expiratory peak PK2. The third phase is the respiratory pause from the end of T3 to the end of T4 which is the time from the end of an active inspiration to the beginning of the next inspiration. T1–T4 are monitored by the microprocessor 75. T1 is a measure of inspiratory rise time and is a sub-component of the active phase of inspiration. It represents the inspiratory rise time to a nominal 75% of peak value. T2 is the active inspiratory phase time. T3 is the active inspiratory/expiratory phase time. T4 is the length of a single respiratory cycle. In order to monitor these values, the microprocessor 75 needs to find the inspiratory turn point 242, the inspiratory peak PK1, the negative expiratory peak PK2, and the next inspiratory turn point 242a. In general, these points are found by various slope and/or amplitude criterion. Also monitored by the microprocessor are the PK1 and Pk2 amplitude values for each phase. Average values of these variables may be computed and stored in the memory of the apnea treatment device in order to allow any method used to analyze the respiratory waveform or any method used to detect the onset of an apnea to adapt to normal variations in the waveform that may occur during sleep.

During the respiratory pause, an on-line, moving average baseline slope value is calculated by the microprocessor 75. The baseline slope calculation is an exponentially weighted average of the prior slopes and is calculated by summing the preceding eight slope values which have been multiplied respectively by the weighting factors ½, ¼, ⅛, 1/16, 1/32, 1/64, 1/128, and 1/256. The inspiratory turn point 242, 242a is then defined as that point where the baseline slope is positive and the realtime slope exceeds the baseline slope by a preset factor. This factor may be, for example from about 1.5× to 5× with a factor of about 2× to 4× being preferred. The slope threshold must be large enough to exclude any cardiac artifact in the respiratory signal 170. Since it is possible that the beginning of the inspiratory phase can be very gradual, a backup threshold criteria is also used to find the point THR1. The threshold is set on every phase to be the amplitude of the last detected negative peak plus one fourth of the exponentially weighted average of the prior peak-to-valley amplitudes. The exponentially weighted average of the prior peak-to-valley amplitudes is calculated by summing the preceding eight peak-to-valley amplitude values which have been multiplied respectively by the weighting factors ½, ¼, ⅛, 1/16, 1/32, 1/64, 1/128, and 1/256. Upon detection of the inspiratory turn point, the stimulus burst is enabled.

Having identified the inspiratory turn point 242, the inspiratory rise time T1 is found by comparing the amplitude of the signal 170 with the calculated amplitude value obtained by taking the amplitude of the last detected negative peak and adding three fourths of the exponentially weighted average of the prior peak-to-valley amplitudes. When the amplitude of the signal 170 exceeds these values, T1 and THR2 have been found. T1 is then compared with stored maximum and minimum values to determine whether the detection of inspiration is genuine. A T1 value that less than the minimum value would typically correspond to a cough, movement or some other transducer artifact. A T1 that is less than the minimum value will cause the stimulus to be disabled immediately as the respiratory signal 170 crosses THR2. This is the slew rate limit discussed above. Where T1 is more than the maximum permitted value, an error in the detection of the inspiratory turn point 242 is probable so that the stimulus will also be immediately disabled. An exemplary minimum value for T1 is 220 milliseconds while an exemplary maximum value for T1 is the exponentially weighted average of T1 from prior respiratory cycles plus 781 milliseconds.

The inspiration time T2 and inspiration peak PK1 are then found at a local maximum of the respiratory signal (i.e. the exponential moving average slope of the respiratory signal goes from positive to negative) with the addition of a hysteresis fall-off past the local maximum to ensure that a peak has been reached (i.e. the exponential moving average slope remaining negative at the fall-off point). An exemplary fall-off would be 12.5% of the exponentially weighted average of the prior peak-to-valley amplitudes. The minimum acceptable value for T2 determines whether the peak is probably an artifact. An exemplary minimum T2 is 750 milliseconds. The maximum acceptable value for T2 determines whether too great a time has elapsed since the turn point to be a valid respiratory signal. The maximum T2 is set according to historical values for T2. For example, maximum T2 could be the exponential moving average of eight preceding T2 values plus 1093 milliseconds. Upon detection of PK1 or the attainment of the maximum permissible T2 value, the stimulus plateau is turned off and the ramp-down of the stimulus commences. As a safety precaution, the total stimulus burst is not allowed to exceed 2.5 seconds. This is the duration limit for the stimulus discussed above.

The inspiration/expiration time T3 and the negative expiratory peak PK2 are then found at a local minimum amplitude with the addition of a hysteresis amount equal to ensure that a negative peak has been reached. An exemplary hysteresis amount would be 2.125% of the exponentially weighted average of the prior peak-to-valley amplitudes. T3 is checked to determine whether it has reached a minimum acceptable value. An exemplary minimum T3 is 1000 milliseconds. The maximum acceptable value for T3 is set according to historical values for T3 and if T3 is beyond the maximum, the stimulus will be disabled for subsequent phases until an acceptable, artifact-free respiratory phase is identified. For example, maximum T3 could be the exponential moving average of eight preceding T3 values plus 1406 milliseconds.

The respiratory cycle period T4 represents the breath-to-breath interval from the last inspiratory onset (n–1) to the present inspiratory onset (n). As with other waveform parameters, T4 is exponentially averaged. This averaged value is used as an adaptive parameter to predict the onset of the next breath. Therapeutically, it is important that the stimulus burst onset be as close to the physiological inspiratory onset as possible. Intrinsically, in a normal subject, the EMG activity of the pharyngeal muscles precede the onset of diaphragmatic EMG activity. The early pharyngeal activity in essence prepares the patehey of upper airway to withstand the negative pressure created during inspiration. Therefore, a predetermined time (e.g. 500 milliseconds) can be subtracted from the average T4 value to predict the next breath and enable stimulation in synchrony with inspiratory effort. Thus, stimulation is preferably enabled by: (1) the expected commencement of inspiration as computed from the T4 average or (2) the detection of a valid inspiratory turn point if that occurs earlier than the computed time for the expected commencement of inspiration.

Initialization of the respiratory signal analysis process occurs when the system is turned on or reset. Initial default values are provided for T1–T4 and an initial period for baseline calculation/signal assessment and offset/gain adjustment is commenced. For example, default parameters can be set as follows: T1=1500 milliseconds, T2=2500 milliseconds, T3=3750 milliseconds and T4=12 seconds. During an initial period of operation, stimulus is suppressed (e.g. for about 60 seconds) while the system develops baseline data about the waveform. The baseline data includes data about the average signal that is being received and its overall amplitude. The system uses this data to set the respiratory signal into the center of the detection range. For example, four (4) eight second baseline averages of the waveform are calculated and are exponentially averaged. This value can be used to adjust the baseline of the signal into the center of the detection range of the analog/digital converter (i.e. an average output of 128 in the range of 0–255). Thereafter, the signal is monitored by further eight second exponential averages and adjusted as required to keep it centered. The amount of gain for the signal is also initially set by taking the highest and lowest peak values detected during an eight second period and then roughly adjusting the gain to prevent clipping and to avoid a signal that is too small. Thereafter, the gain is controlled by calculating an exponential average of the preceding eight positive and negative amplitude peaks differentials detected in the signal and using that average to adjust the amplifier gain to cause the signal to cover about 80% of the range of the analog/digital converter. This is accomplished by testing the average value against maximum and minimum criteria and incrementing and decrementing the gain control to keep it within a preset maximum and minimum.

Figure 19:
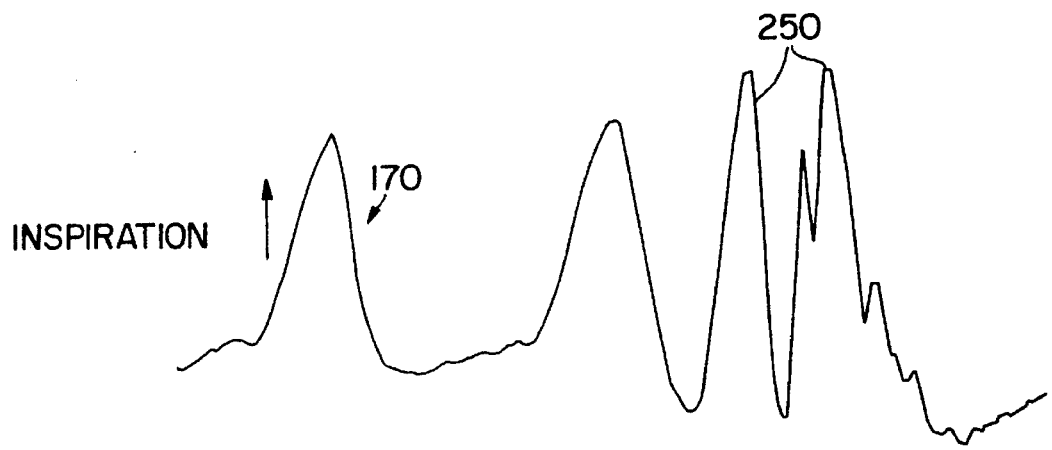
FIG. 19 is a respiratory waveform according to FIG. 18 with a cough artifact.
Figure 20:
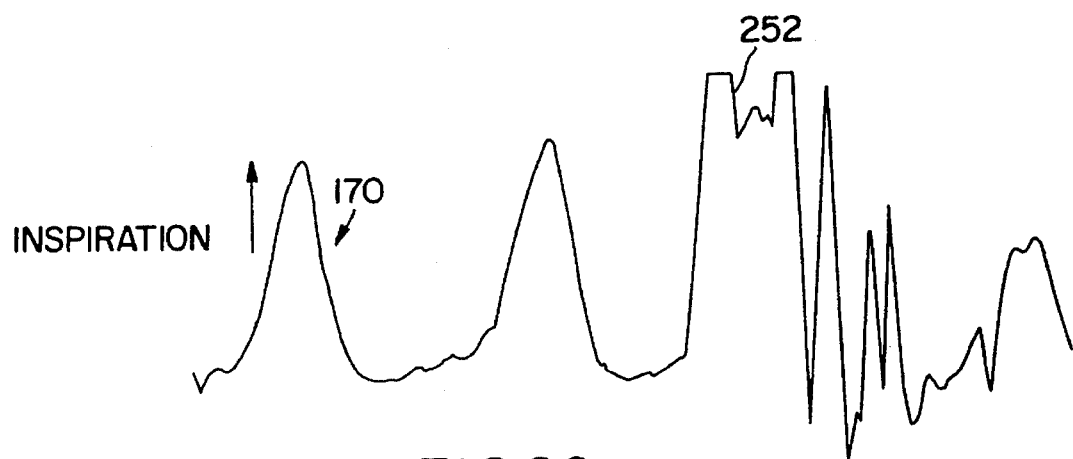
FIG. 20 is a respiratory waveform according to FIG. 18 with a movement artifact.

Therefore, when the respiratory signal 170 contains a cough artifact 250 such as that shown in FIG. 19 or a movement artifact 252 such as that shown in FIG. 20 the waveform analysis described above will differentiate the form of the artifacts from the more regular form of normal inspiration and ensure that those artifacts will not trigger inappropriate stimulation. In the event that a long series of invalid respiratory cycles are encountered, the stimulus is terminated and the system goes through a new calibration cycle to attempt to synchronize with an artifact-free signal.

The same waveform analysis can also provide an indication of the onset of apnea in the patient in order to identify the proper time to turn on stimulation or to determine whether stimulation is being effective in producing a patent airway. In an ideal diagnostic setting, obstructive apnea detection involves measuring a respiratory effort in the absence of airflow. However, in an easy-to-use therapeutic or an implantable device, an airflow measurement is not easily arrived at. Therefore, respiratory effort is used to identify the onset of an apnea episode. For example, at the onset of an apnea, an airflow measure 260 as shown in the graph of inspiratory volume of FIG. 21a shows a normal airflow peak 262 followed by diminishing peaks 264, 266 and 268 and a return to normal air intake at peak 270. The comparison respiratory signal 170 from FIG. 21b shows the opposite situation with respiratory effort being normal at peak 272 while the obstructed airway causes the patient to progressively increase respiratory effort at peaks 274, 276 and 278 in an attempt to obtain air. At peak 280, the patient has aroused himself slightly in response to the apnea, allowing the airway to open for a normal breath. The waveform analysis set forth above can measure the PK1 to Pk2 amplitude and other parameters of the respiratory effort waveform shortly after the device is turned on to establish a baseline value for normal, unobstructed breathing. These values can then be stored in memory and compared with the same parameters in each respiratory cycle to identify the increased inspiratory effort above a predetermined threshold value that is characteristic of an apnea event. The threshold value can be programmed into the device according to the requirements of the particular patient. Upon detection of the onset of the apnea event, stimulation can then be enabled to restore the airway to patency or the stimulation intensity can be increased if the intensity of stimulation being given has been inadequate to produce patency.

The waveform analysis can also be used to detect arousal of the patient. In a diagnostic setting, an arousal is clinically determined using EEG, EOG and EMG signals. An awakening arousal is in essence a sleep stage. These signals are not readily available in an easy-to-use therapeutic device or implantable device. However, an analysis of cough and movement artifacts in the respiratory waveform can give an indication of arousal. A respiratory waveform with a typical cough artifact is shown in FIG. 19 and a typical movement artifact is shown in FIG. 20. The values for T1–T4 and PK1 and Pk2 would indicate that these waveforms are not from regular respiratory activity. In fact, the rapid rise times and frequent positive and negative peaks are characteristic of body movement during periods of arousal. Therefore, multiple detected T1–T4 values that are shorter than an established threshold value and which are associated with the presence of detected multiple peaks PK1 and PK2 would constitute a detected arousal. This detected arousal could be used to delay the onset of stimulus until the patient has returned to sleep. An activity sensor such as that used in heart pacemakers can also be included in the device and then used to determine arousal of the patient. For example, a signal from the activity sensor can be monitored and if predetermined amplitude and duration thresholds are satisfied, that would constitute a detected arousal. For even greater accuracy in detecting arousal, the activity sensor arousal determination can be combined with the respiratory waveform detected arousal. For example, if both the activity sensor and the respiratory waveform indicate arousal, then the stimulation to the patient is disabled. The threshold values for arousal determination for both the respiratory waveform and the activity sensor can be pre-programmed into the device according to the sleep activity of the particular patient.

Figure 22A:
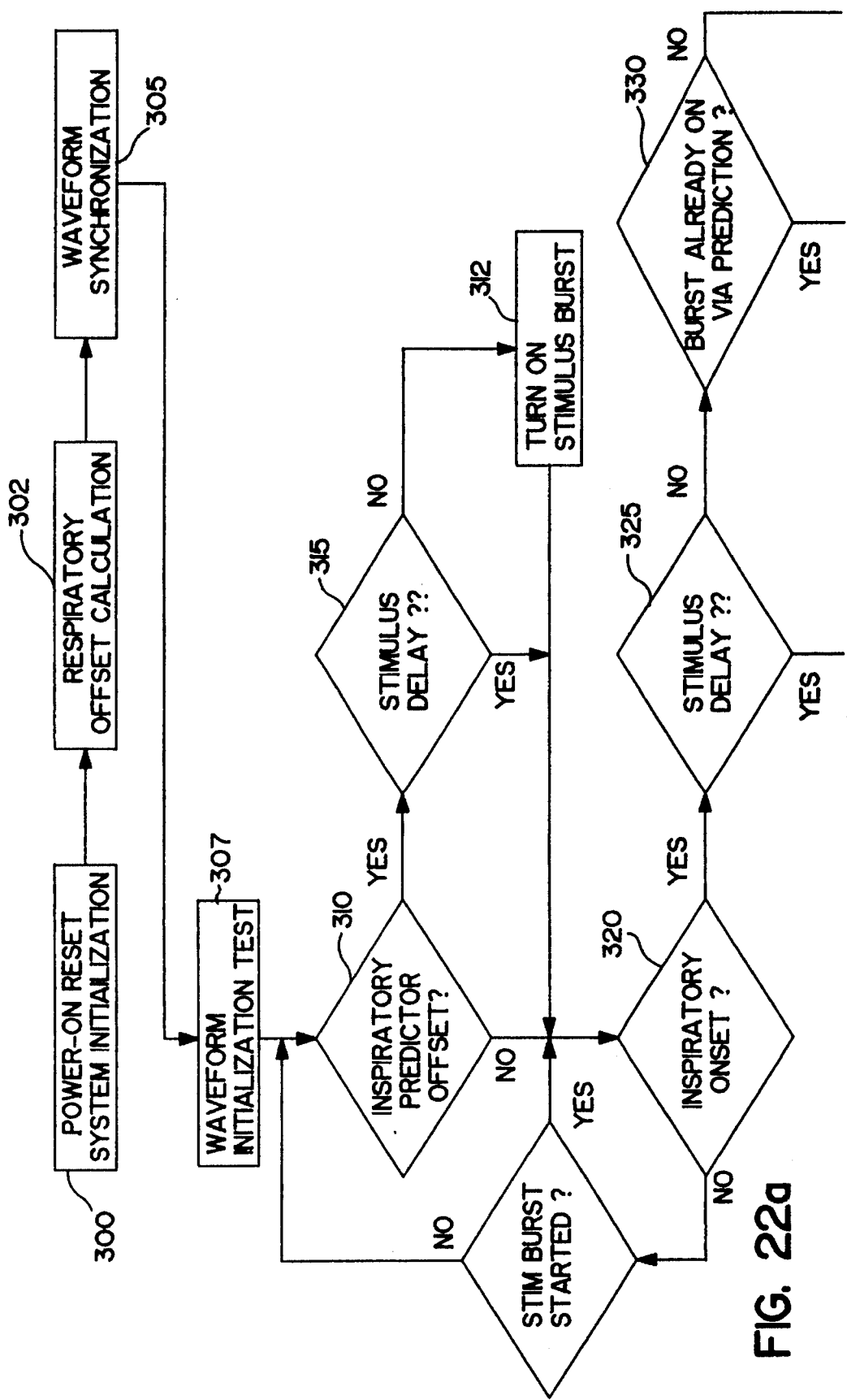
FIGS. 22a–c is a block diagram for the analysis of the respiratory waveform and initiation of stimulation according to the device of FIG. 6.
Figure 22B:
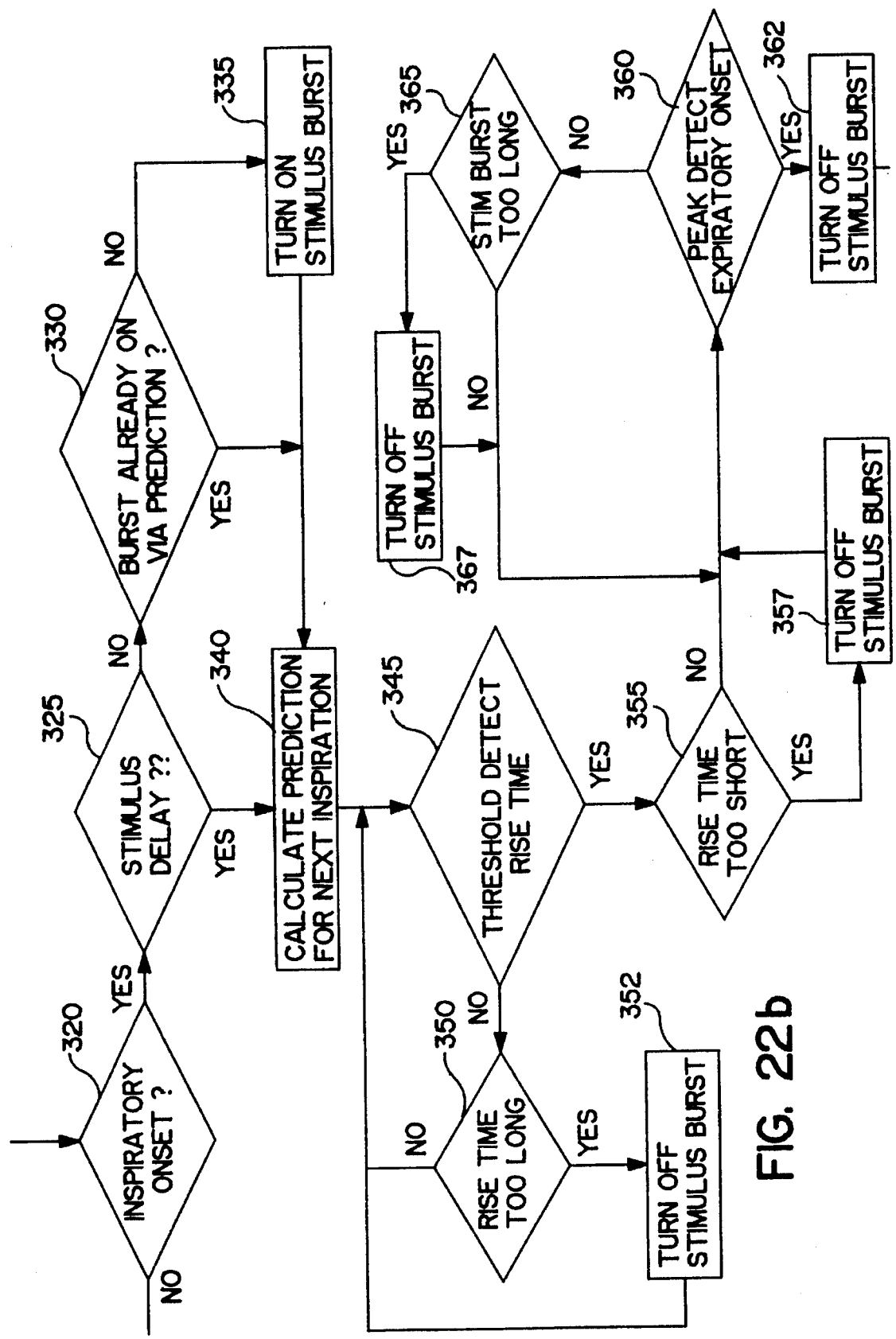
Figure 22C:
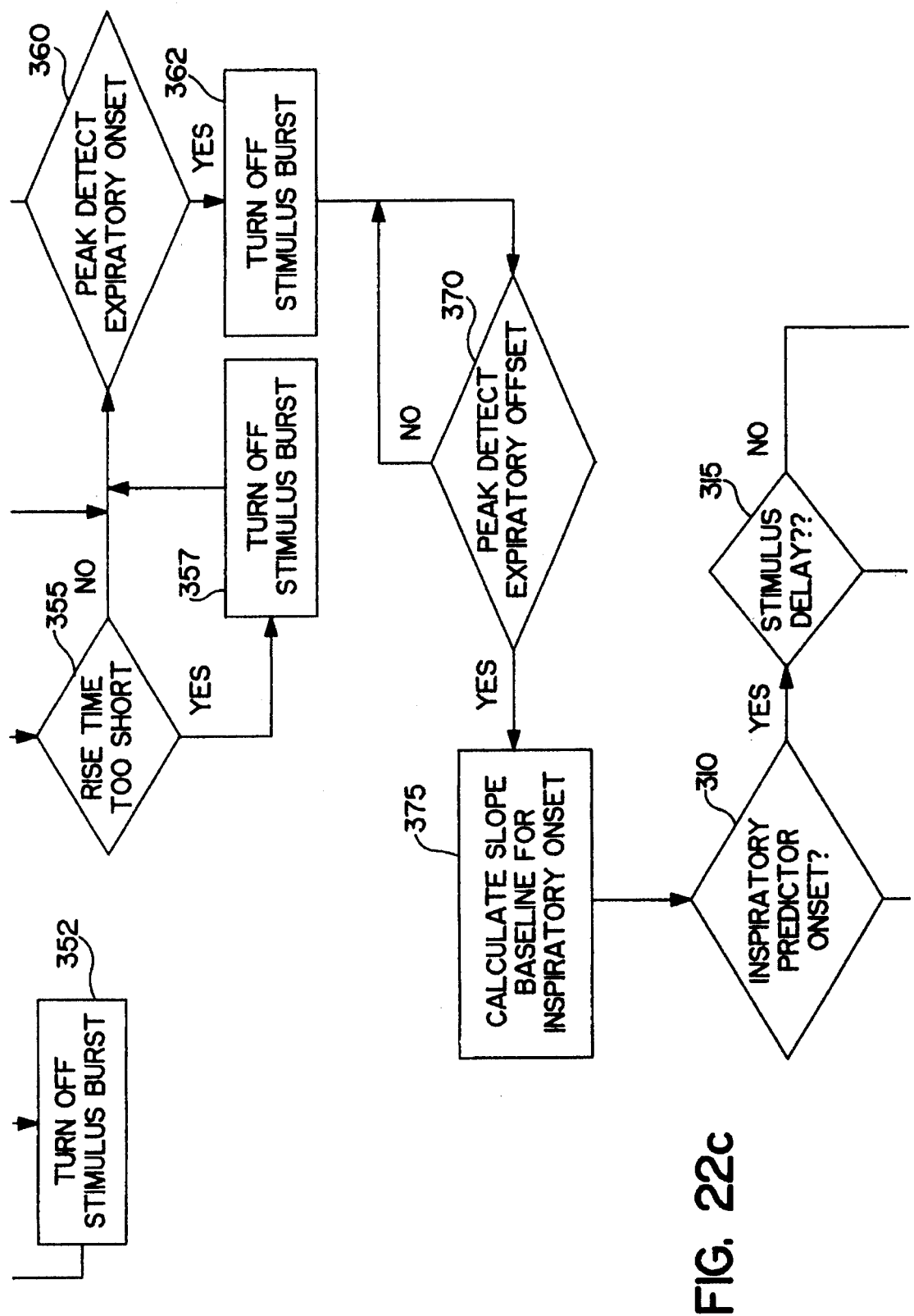

The block diagram of FIG. 22a–c summarizes the basic method for inspiration detection and stimulation in response to inspiration detection. In general, a baseline amplitude and offset calculation is established for the respiratory effort waveform. The waveform is then tracked from the inspiratory onset (i.e. achievement of the inspiratory turn point) to expiratory onset (i.e. achievement of the inspiratory peak PK1) and to expiratory offset (i.e. the achievement of the negative expiratory peak PK2). An adaptive time/morphology filter is used to adjust to normal changes in the respiratory pattern. An average of preceding breath-to-breath intervals is used to provide a predicted onset for the next breath such that the stimulus can be activated in synchrony with the predicted onset and thereby slightly precede the actual breath. In the event that the breath is earlier than predicted, stimulation is commenced upon detected inspiration onset. Initialization 300 of all system peripheral inputs and outputs occurs upon a power-up of the system or when a manual reset is activated. A respiratory offset calculation 302 is undertaken by sampling the waveform and finding an average offset for the DC coupled amplifiers. The system then synchronizes 305 itself to the waveform by detecting an expiratory offset. The system then undergoes an initialization step 307 in which the system tracks several respiratory cycles to set the amplifier gain and establish the normal morphological parameters for the waveform. A time reference is also established with respect to the last inspiratory onset so that the a predicted onset can be calculated for the next breath. The system then determines whether the appropriate amount of time has elapsed for a predicted onset 310. If yes, the requirement for stimulus delay 315 is tested and if delay is not required, the stimulus is enabled 312. If no, the waveform is tested for detection of inspiration onset 320. If yes for inspiration onset detection, the requirement for stimulus delay 325 is tested as well as a test for whether the stimulus is already enabled 330. If those tests are met, stimulation is enabled 335 and the next predicted onset time is calculated 340. After detection of inspiratory onset 320, the amplitude threshold value (THR2) and rise time (T1) are calculated 345. If the rise time is found to be too long 350 stimulation is disabled 352 since the detected inspiration onset is probably an invalid onset detection. Similarly, if the rise time is found to be too short 355 stimulation is disabled 357 since the detected inspiration onset is probably an invalid onset detection. The system then looks for the expiration onset (PK1) 360 and when detected the stimulus is disabled. If not detected the time of stimulation is checked 365 and if it is too long, stimulation is disabled 367. Once the expiratory onset (PK1) has been identified, the system looks for expiratory offset (PK2) 370. Once expiratory offset detected, the system begins to calculate the slope baseline 375 so that the next inspiratory onset can be found. The system then begins a new cycle by again testing for the predicted inspiratory onset 310.

Figure 23:
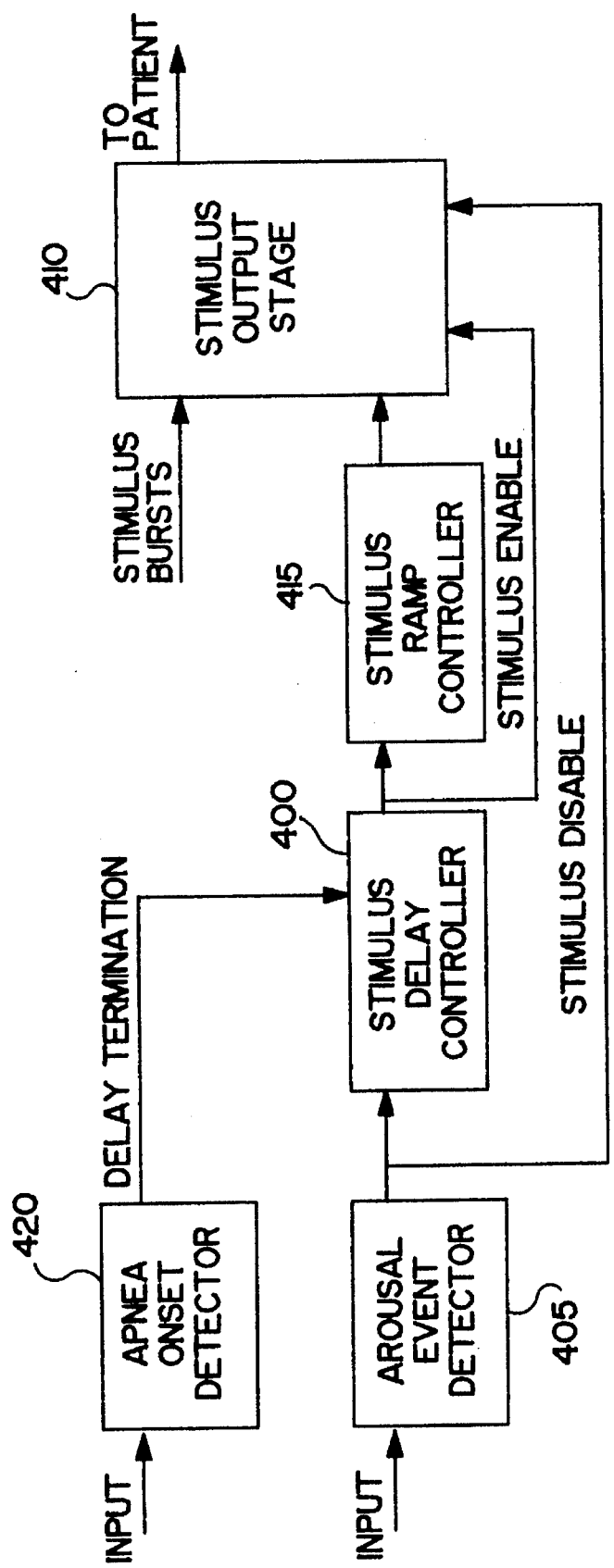
FIG. 23 is a block diagram for the operation of the device of FIG. 6 in response to arousal of the patient.
Figure 24:
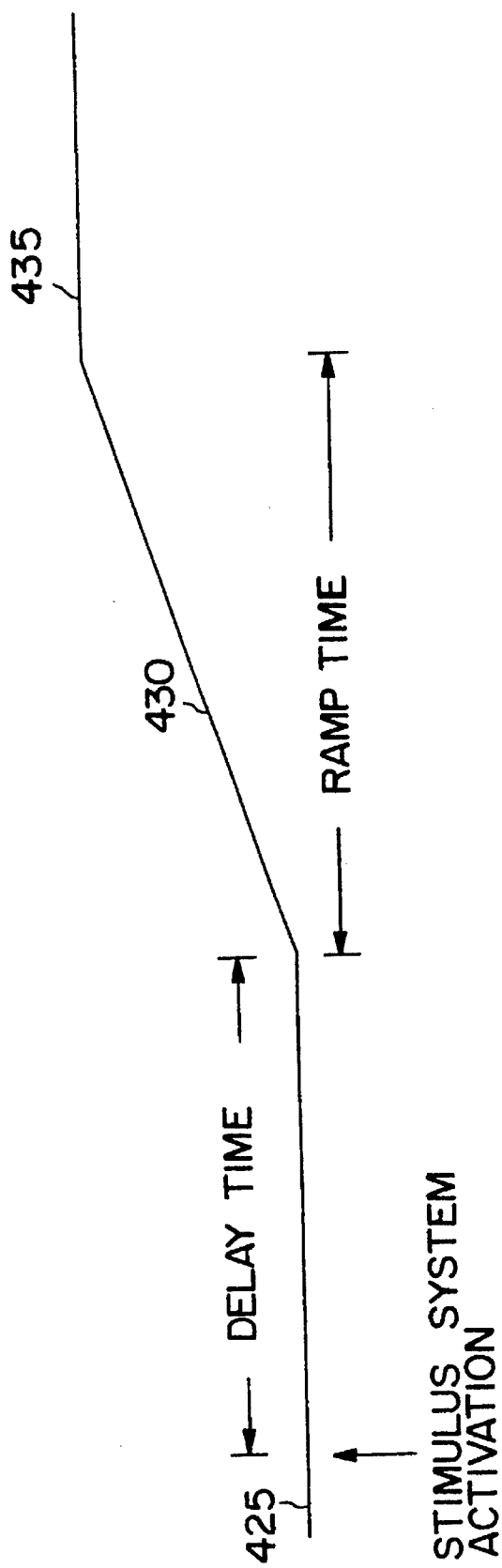
FIG. 24 is an amplitude ramping and delay function activated in response to patient arousal according to FIG. 23.
Figure 25:
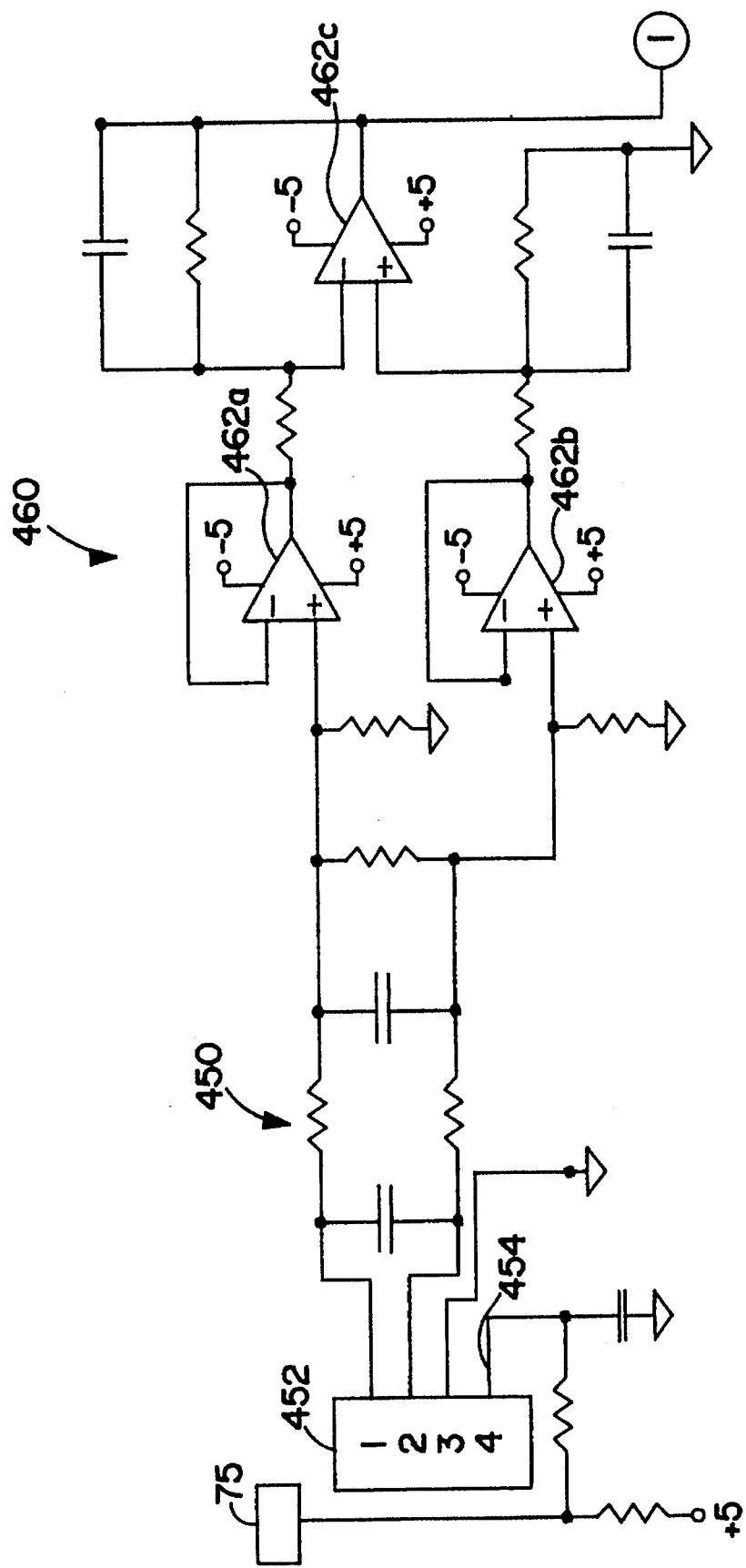
FIG. 25 is a diagram of a circuit for filtering and amplifying the respiratory effort signal of the device of FIG. 6.
Figure 26:
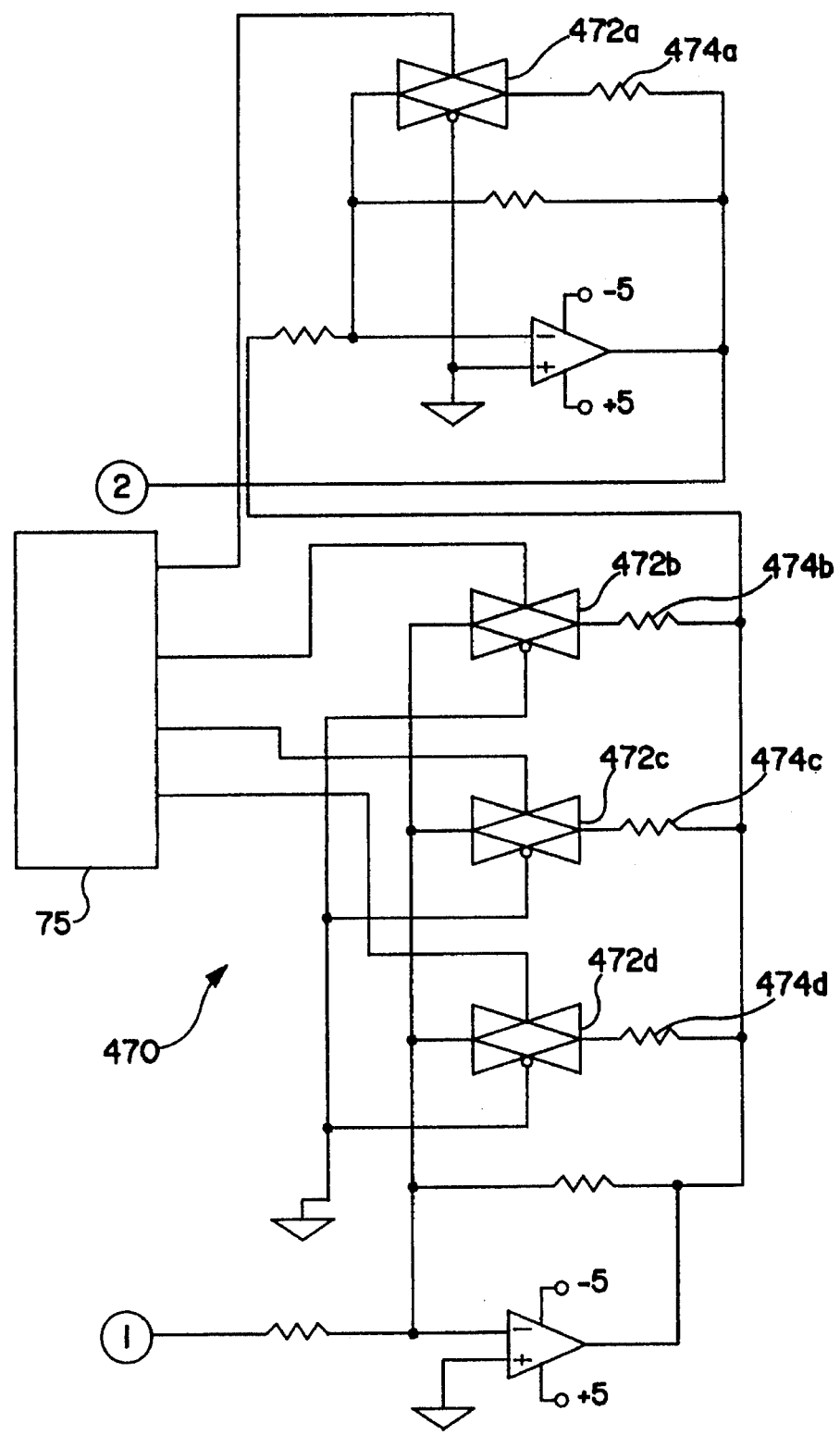
FIG. 26 is a diagram of a circuit for the gain control of the device of FIG. 6.

Since stimulation of the upper airway can have very distinct sensations that disturb the patient, it is very important that the patient is allowed to get to sleep before the onset of stimulation and, if aroused, is able to return to sleep without feeling the effects of stimulation. This is accomplished by the stimulus delay system shown in FIG. 23. A stimulus delay controller 400 receives an arousal signal from the arousal event detector 405. The arousal event detector 405 can be movement detected through the waveform analysis as set forth above or it can be any other event that would be indicative of an arousal. For example, the patient may press the reset button or may turn the unit off and on to manually indicate that he is awake and wishes to delay stimulation. Or, as described above, the device itself may contain an activity sensor that responds to body movement similar to those used to detect patient activity in heart pacemakers such as the piezoelectric sensor disclosed in U.S. Pat. No. 4,428,378 issued to Anderson et al or the position sensor used in a neurostimulator as disclosed in U.S. Pat. No. 5,031,618 issued to Mullett which are incorporated herein by reference in their entirety. The signal from the arousal event detector 405 is received by the stimulus delay controller 400 and at the same time sends a signal to the stimulus output stage 410 which disables the stimulus. The stimulus delay controller 400 must then determine when and in what manner to resume stimulation. For example, in response to being turned on, the stimulus will be completely suppressed for the initialization phase for the unit (typically about 60 seconds) and then suppressed for a period of time ranging from 0 to 20 minutes which is preprogrammed into the unit according to the needs of the patient. For example, a delay of 15 minutes may be used to allow the patient to get to sleep initially. Or, if the reset button is pushed, a second, preprogrammed delay (which is typically shorter than the power-on delay) would be activated which also suppresses the stimulation. For example, a 1 to 5 minute delay may be sufficient for a sleepy patient. While it may be convenient to completely suppress the stimulation during the delay period, it is only necessary to reduce the level of stimulation to a stimulation that is below the level of physiological response that is perceptible to the patient. Reducing the level of stimulation without suppressing it completely can be accomplished by activating a stimulus ramp controller 415 which, when activated, reduces the stimulus amplitude to a very low value and gradually increases it over a preselected period of time so that at the end of that time, the stimulus provided will be the full stimulus amplitude programmed into the device. For example, the stimulus could be ramped up over a 30 to 60 second period depending on the presumed degree of wakefulness of the patient. Either a delay with complete stimulus suppression or a ramped stimulus can be used as desired by the patient. As shown in FIG. 24, in a preferred delay system, the delay with complete stimulus suppression 425 is combined with the ramp controlled stimulus 430 until the full programmed amount of stimulus 435 is achieved. Also, in a preferred embodiment, the stimulus delay controller records and responds to one or more parameters characteristic of wakefulness of the patient such as the frequency of arousal events, the intensity of an arousal event or the duration of an arousal event so that if the arousal parameter or combination of parameters meets preprogrammed criteria, the delay period is automatically adjusted. Thus, for short, frequent arousal periods of low intensity (such as the patient turning over in his sleep), it can be assumed that the patient is very sleepy and only a short delay is provided (e.g. about 1 minute with a 30 second ramp time) while in the case of longer duration arousal events or more intense arousal events (such as the patient getting out of bed), it can be assumed that the patient is wakeful and a longer delay is provided (e.g. about 5 minutes with a 60 second ramp time). The selection of particular parameters or combination of parameters will depend on the methods chosen to detect arousal and can be readily adjusted by those skilled in the art by testing in patients according to the principles set forth above. Preferred parameters include those which may be derived from the analysis of respiratory waveforms as set forth above and activity sensing as practiced in activity-responsive heart pacemakers.

In one embodiment, five sources of arousal information would be employed in the system to trigger the arousal event detector 405: power-on reset, manual reset, position sensor, respiratory waveform, and activity sensor. Monitoring of all of these parameters along with controlling stimulation delay can be handled by the microprocessor 75. The power-on reset is activated at the time the patient retires to bed and causes a 15 minute delay in the stimulus delay controller 400. The manual reset is activated by the patient to indicate arousal and causes a 5 minute delay to be provided by the stimulus delay controller 400. The position sensor is mounted on the respiratory belt where it can determine the position of the patient's upper body (i.e. whether the patient is in a recumbent or upright posture) and determines whether the patient's position has changed from a recumbent position to a sitting or standing position. Upon detection in a change to a standing or sitting posture, arousal is detected and an 8 minute delay is applied by the stimulus delay controller 400. The respiratory waveform is monitored with respect to the rise time T1 with the calculation of a moving exponemial average rise time. When the average rise time falls below 250 milliseconds, arousal is assumed and the stimulus delay controller 400 provides a one minute delay. The piezoelectric activity sensor is also mounted on a surface of the respiratory belt in order to indicate the activity of the patients' body. The sensor generates a sensor output due to deflection of the surface on which it is mounted as compression waves from movement of the patient cause that surface to deflect. The output of the activity sensor is monitored for changes in patient movement. This can be done by first monitoring the output of the activity sensor and computing four eight second average levels for sensor output at one minute intervals sixteen minutes after power-on reset and averaging the four eight second averages as a baseline activity level for the patient. Thereafter, the sensor is monitored approximately every second and an exponential moving average of the sensor output is computed. When the average output reaches a preprogrammed level (e.g. 3–5 times the stored baseline level), arousal is presumed and a 30 second delay is applied by the stimulus delay controller 400. The output of the stimulus delay controller 400 is also determined by the interrelationship between the arousal detection parameters. For example, during the 15 minute delay following power-on reset, if a manual reset is detected, the controller 400 will provide the longer of the remaining 15 minute delay provided by the power-on or the 5 minute delay provided by the manual reset (i.e. the longer delay will always be favored). In addition to the delay periods set forth above, the delay provided in response to the detected arousal from the respiratory waveform and activity sensor is adjusted based on number of arousal detections, the duration of the sensed arousal and the time between sensed arousals. For example, if arousal is detected by both respiratory waveform and activity sensor for more than 15 seconds, a major arousal is assumed and a two minute delay is provided by the controller 400. On the other hand, if the activity sensor alone indicates multiple short arousal periods (e.g. 3–5 arousals 3–10 seconds apart), it can be assumed that the patient is merely sleeping restlessly and the delay provided by the controller 400 in response to the activity sensor can be reduced to 10 seconds. Further, since the device described is programmable, the various delay times and other parameters of the system as set forth in the example above may be default values for the device which may be programmed to different settings by the prescribing physician.

In the event that the patient returns to sleep prior to the completion of the delay, the system can monitor for an apnea event and resume or increase the stimulation in response to the detection of obstructive sleep apnea. For example, in one embodiment, the peak-to-peak amplitude of the respiratory effort waveform is monitored and an exponential moving average of amplitude calculated. When the amplitude in each of three successive respiratory cycles exceeds the average amplitude by 10%, an apnea is assumed and the delay controller 400 cancels the delay, thereby allowing stimulation to be enabled. To prevent false apnea detection, the device could be programmed to maintain the delay after the first detected apnea until the detection of one to three additional apnea episodes (as programmed into the device) over a 3–5 minute period confirms the detection of the apnea.

Figure 27:
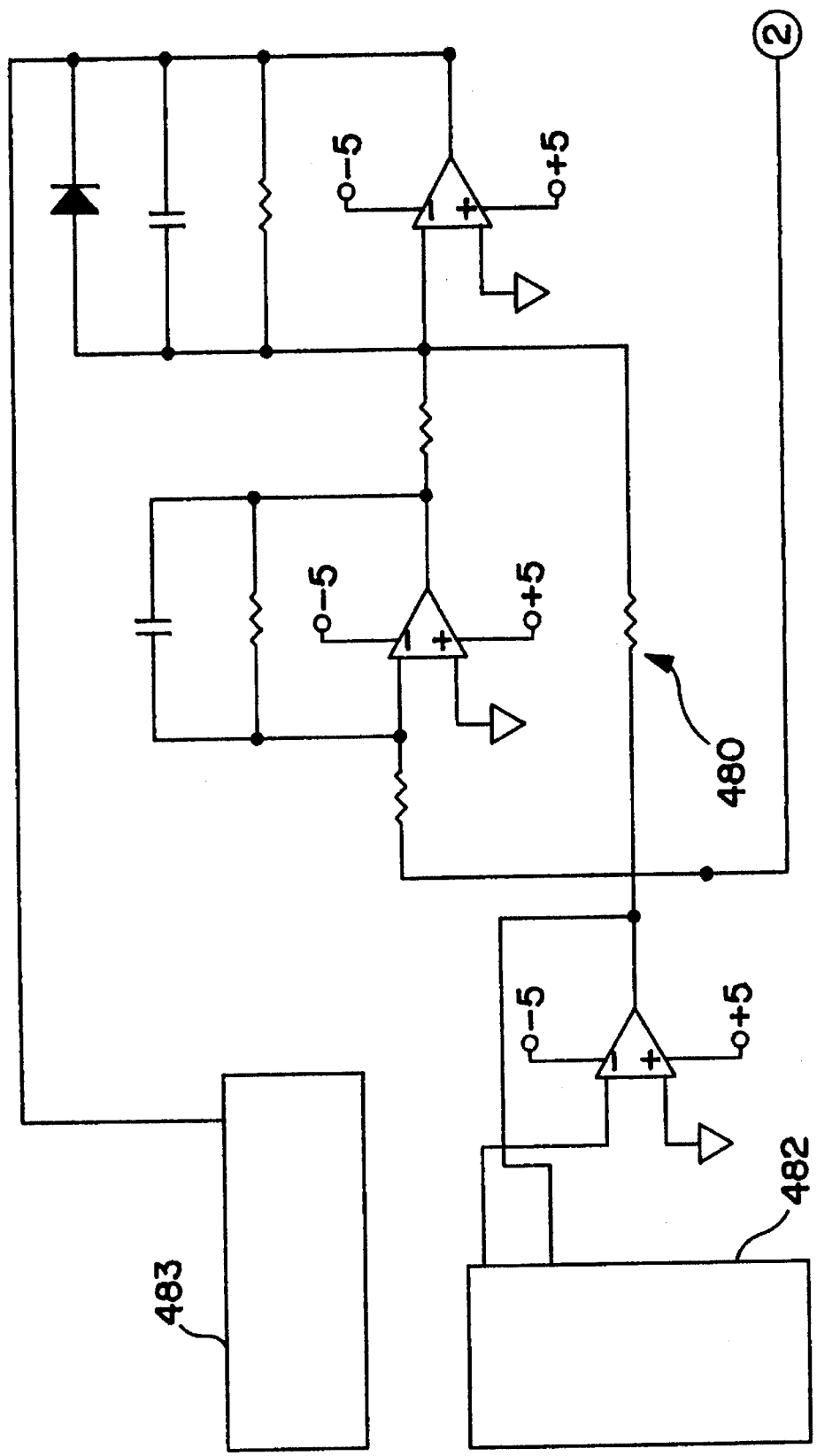
FIG. 27 is a diagram of a circuit for the A/D converter of the device of FIG. 6.
Figure 28:
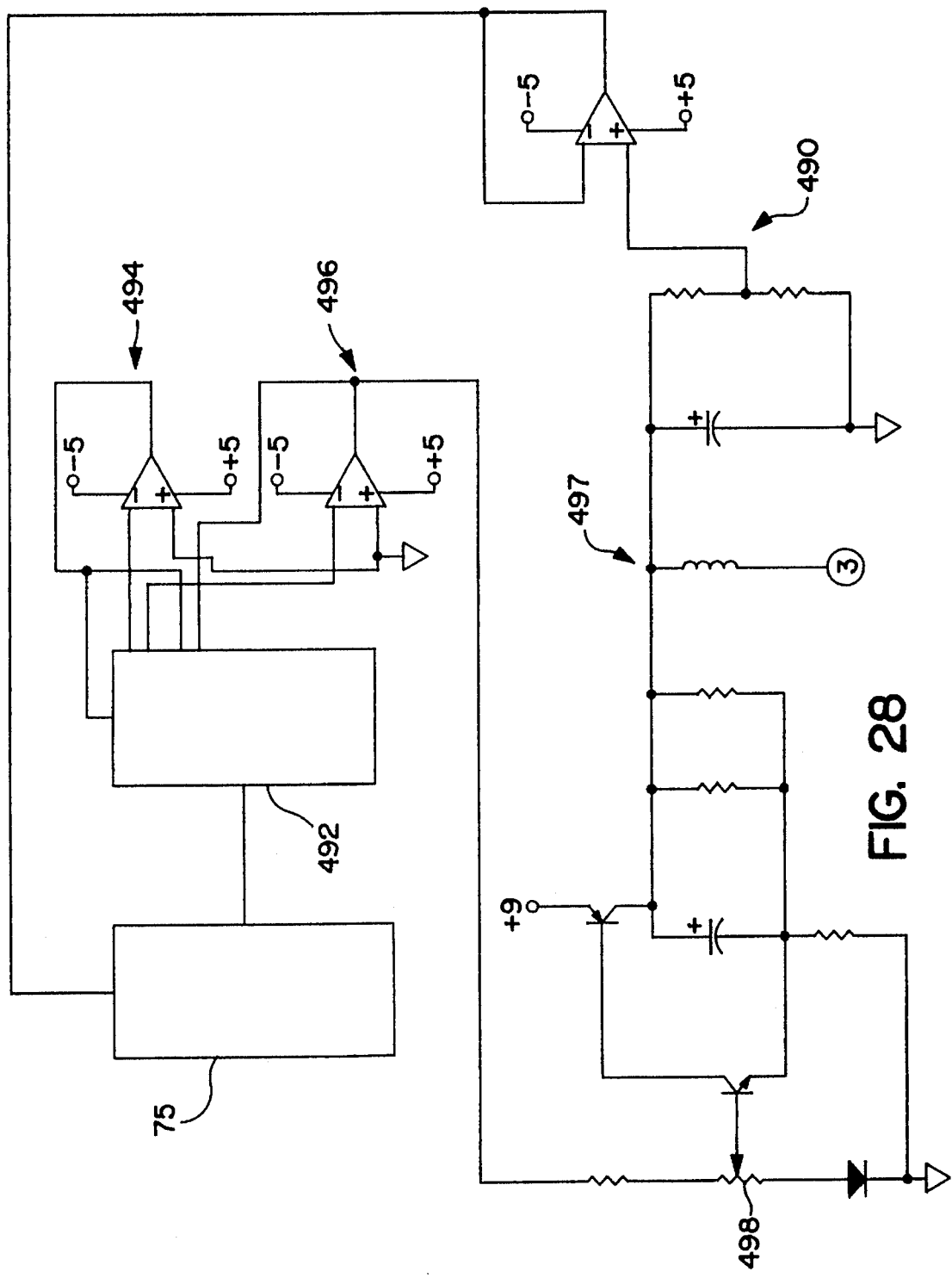
FIG. 28 is a diagram of the D/A converter and stimulus shaper of the device of FIG. 6.
Figure 29:
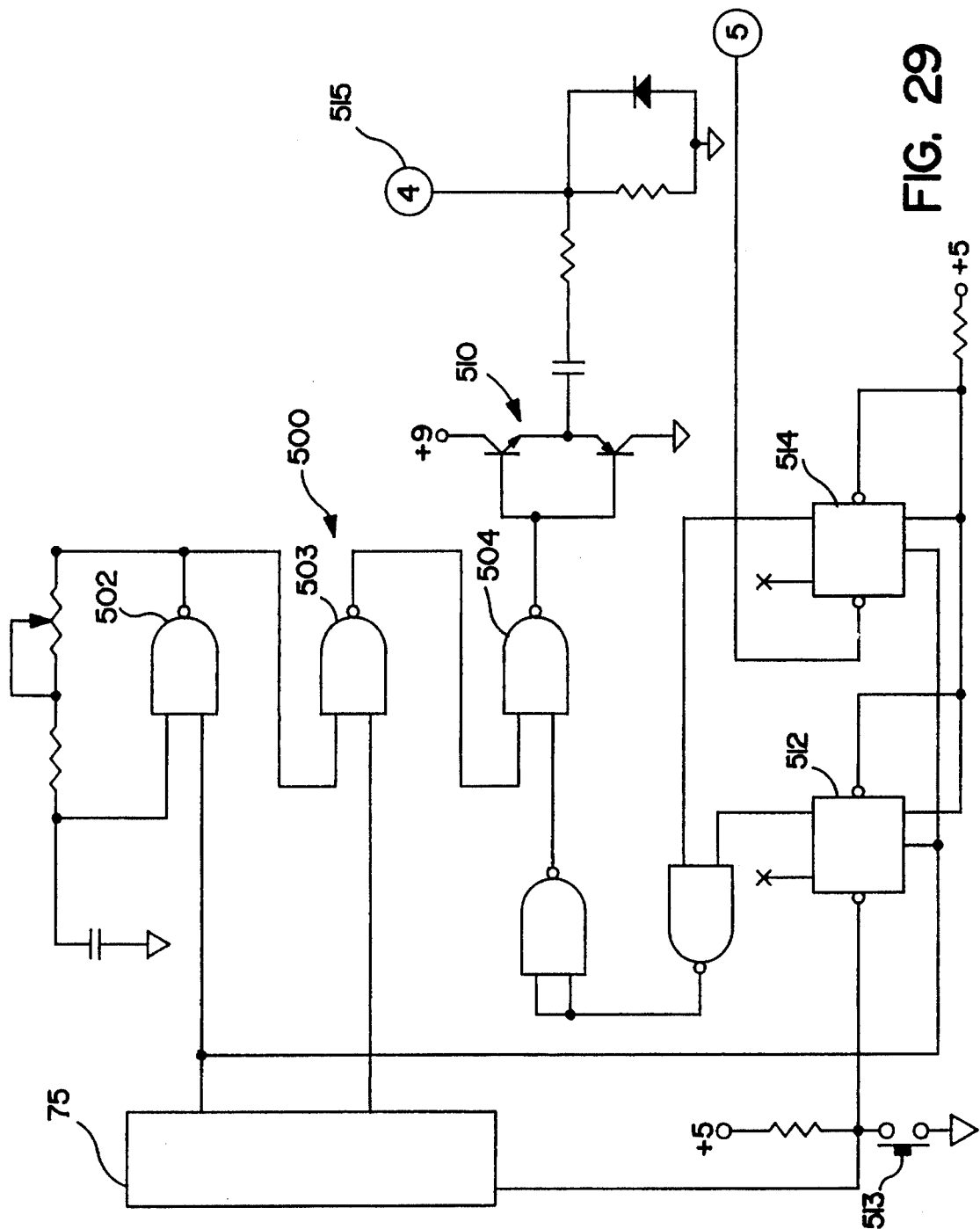
FIG. 29 is a diagram of the RF oscillator of the device of FIG. 6.
Figure 30:
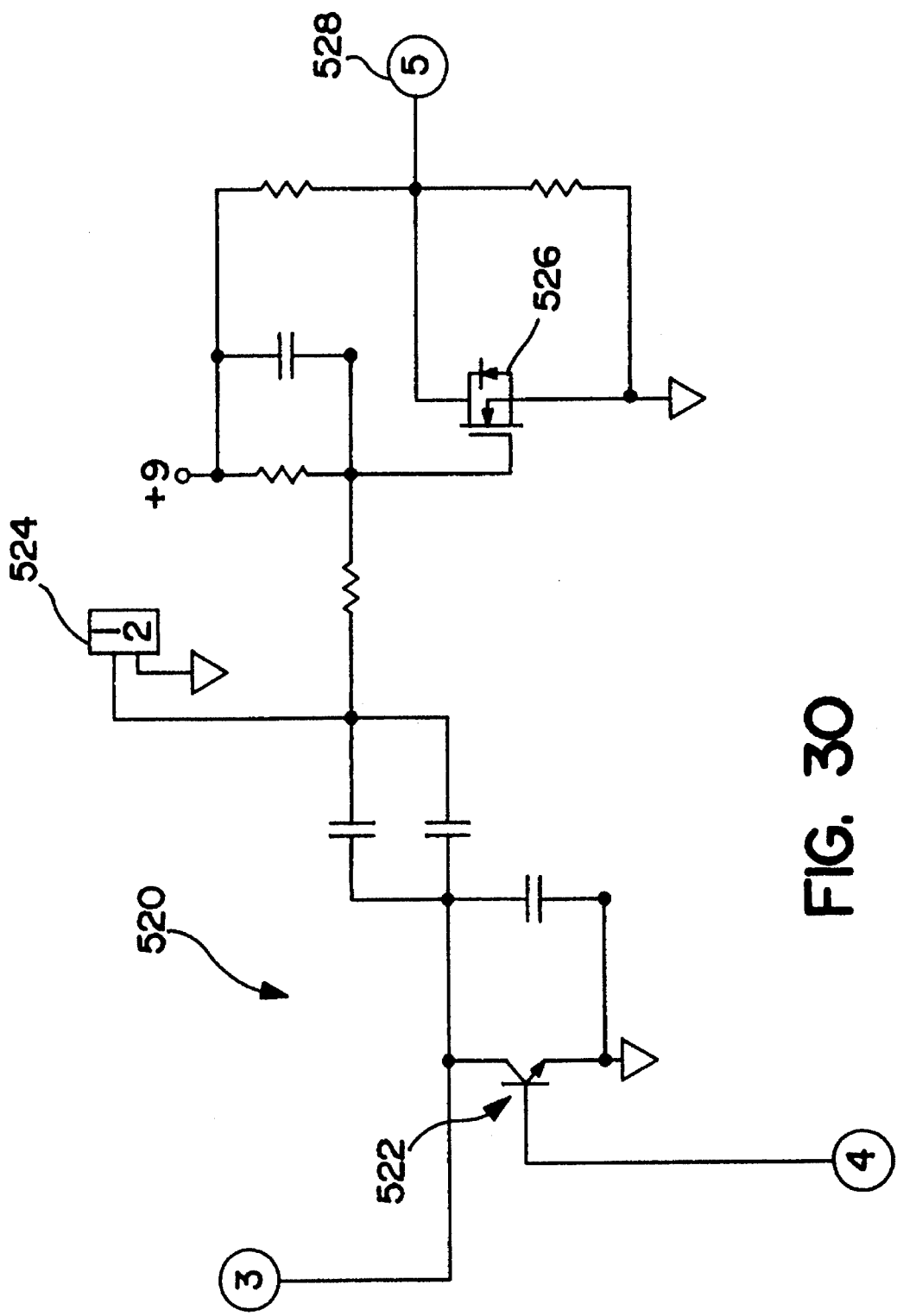
FIG. 30 is a diagram of the antenna output of the device of FIG. 6.
Figure 31A:
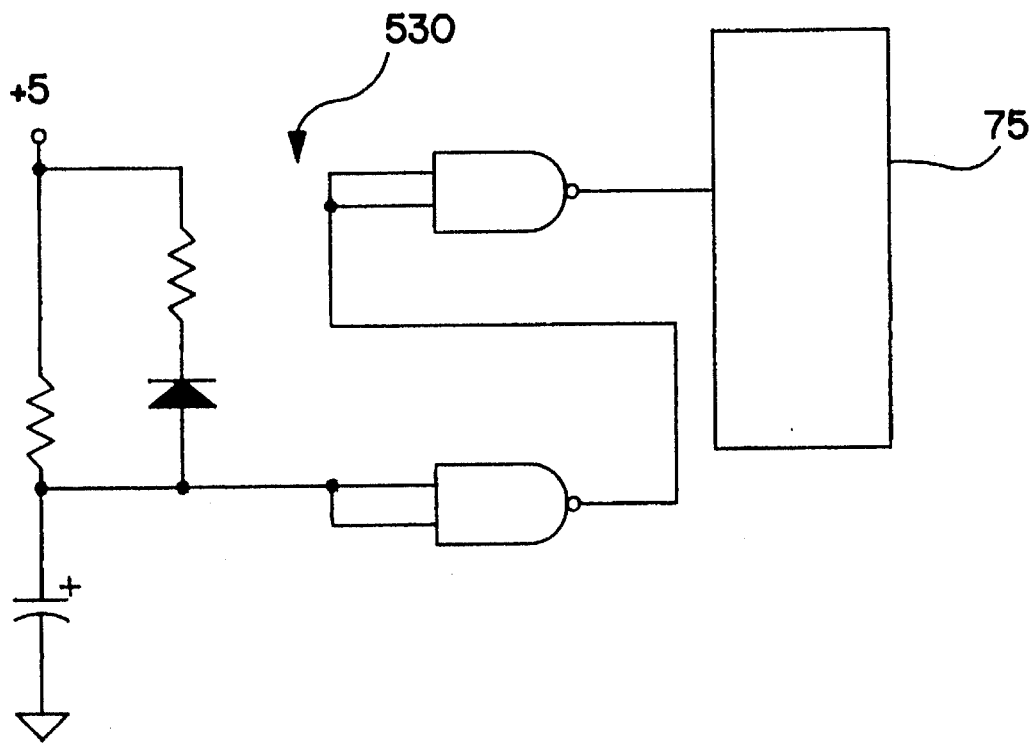
FIGS. 31a and 31b are diagrams of operable resets of the device of FIG. 6 including power-on reset (FIG. 31a) and manual reset (FIG. 31b)
Figure 31B:
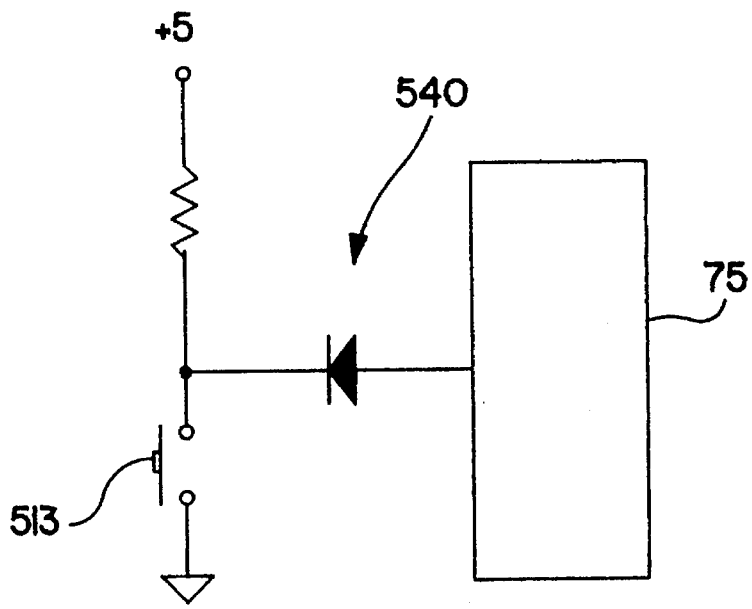
Figure 32:
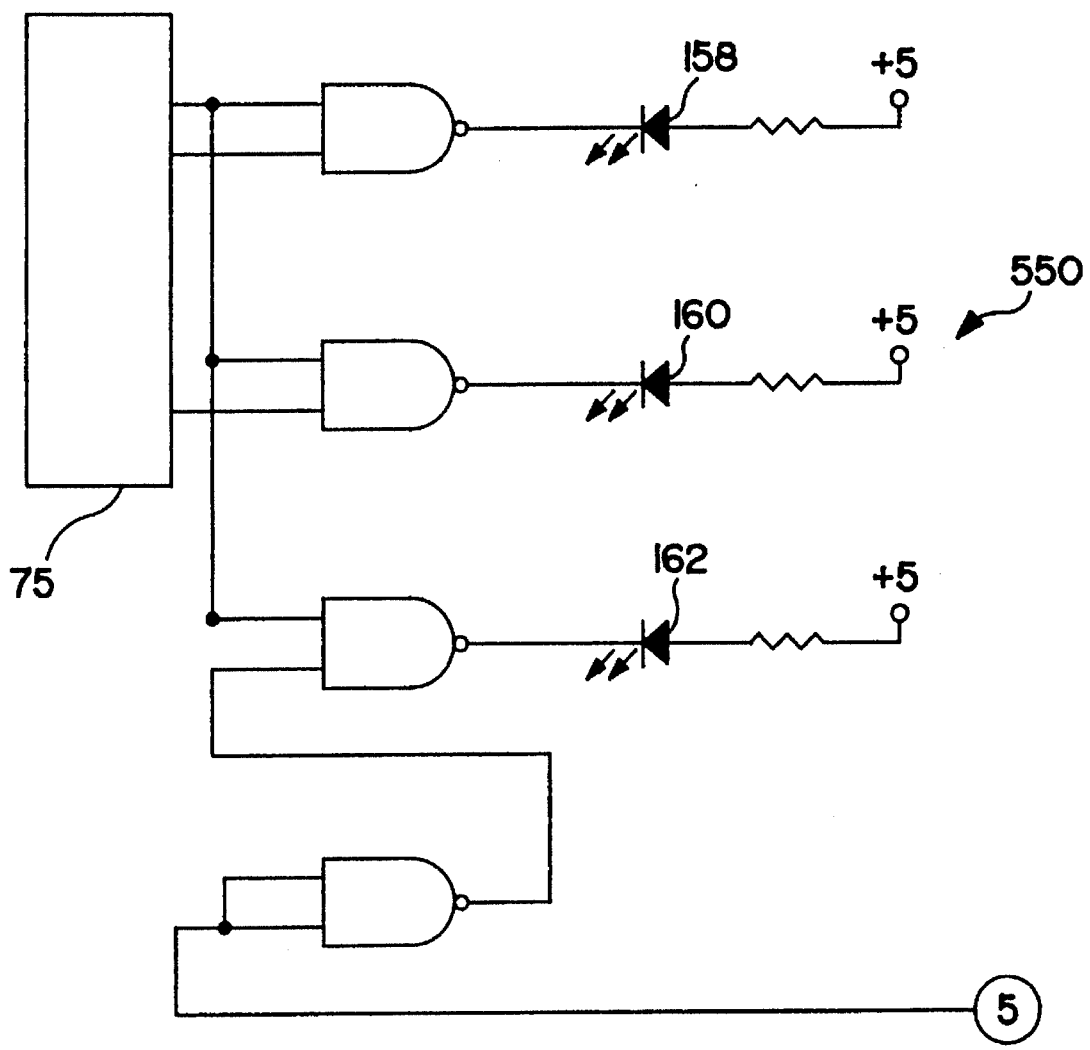
FIG. 32 is a diagram of circuit for the panel indicators of the control panel of FIG. 8.

Referring now to the circuit diagrams of FIGS. 25–32, FIG. 25 shows a low pass filter 450 and a differential low pass amplifier 460 for processing the transducer signal that is received through a four pin connector 452. One line from the connector 454 is connected to the microprocessor 75 in order to indicate that the transducer is properly connected. Quad op amps 462a, 462b, 462c are used in the amplifier 460. The signal output from the amplifier 460 goes to the gain control 470 shown on FIG. 26. The gain control 470 is operated by the microprocessor 75 which selects one or more of the quad analog switches 472a, 472b, 472c, 472d to be activated. Resistors 474a, 474b, 474c 474d are thereby selected or deselected from the circuit as required by the microprocessor 75. The resistors 474a–d each have different values so that their selection or deselection from the circuit causes the gain of the signal to be adjusted. The signal output from the gain control 470 goes to the offset control 480 on FIG. 27. Referring now to FIG. 27, the analog offset is generated by the digital/analog converter 482 which is controlled by the microprocessor 75. The resulting amplified and offset respiratory signal is sent to the analog/digital converter 483 where the signal is digitized and sent to the microprocessor 75. The analog/digital converter 483 is used to provide the microprocessor 75 with the information about the waveform such that the microprocessor 75 can control signal gain and offset. The microprocessor samples and averages the respiratory signal from the analog/digital converter 483 over a representative interval (e.g. eight seconds). This calculated average offset is then used to determine the DC offset to be generated through the digital/analog converter 482. Exponentially averaged peak/nadir values for valid respiratory signals are used to determine gain through the microprocessor gain control lines of FIG. 26. FIG. 28 is a diagram of the stimulus shaping circuitry 490 in which a dual digital/analog converter converts the signal from the microprocessor 75 into a monophasic waveform which defines the shape of the stimulus pulse. The first stage of the converter 492 receives a digital signal from the microprocessor 75 defining the shape of the stimulus, including the ramp and plateau portions for the waveform and outputs at a first stage 494 the analog waveform at full gain. The second stage of the converter 496 receives a digital signal from the microprocessor 75 which indicates the gain to be applied and the analog output from the converter reduces the gain of the waveform to its desired level. Voltage level circuitry 497 controls the output level of the RF signal along with the potentiometer 498 (to adjust the maximum value of the stimulus output) and the first and second converter stages 494 and 496. The microprocessor 75 monitors the stimulus level output and compares that level to a preprogrammed stimulus level characteristic of an overvoltage malfunction such that the stimulus output will be disabled if it is exceeded. The output signal from this circuit is used to bias the RF output switching transistor 422 on the antenna output circuit of FIG. 30. Referring now to the RF oscillator circuit 500 of FIG. 29, microprocessor 75 turns on the oscillator by activating gate 502 and also gates the pulse by activating gate 503. Latch 512 disables the stimulus output through gate 504 when the reset switch 513 is pressed. Latch 514 disables the stimulus output through gate 504 when the antenna is removed. After either of these events, the stimulus must be re-enabled by the microprocessor 75. The output signal 515 goes to the antenna output circuit 520 in FIG. 30 where it is combined with the shaped signal from the stimulus shaping circuitry 390 in FIG. 28. In the antenna output circuit 520, the signals are combined through an NPN power transistor 522 into the desired output signal for the device at the antenna connector 524. To detect the presence of the antenna connection, an antenna detector circuit employing an N-channel FET 526 is used with a signal output 528 to the latch 514 in FIG. 29 and to the LED antenna indicator 162 on FIG. 32. FIGS. 31a and 31b show the patient-operable resets for the device including a power-on reset 530 and manual reset 540 respectively. In the power-on reset 530, powering-up the device causes the reset on the microprocessor 75 to be activated. In the manual reset 540, the patient can press the reset switch 513 to reset the microprocessor 75 and disable the stimulus output via latch 5 14 as shown in FIG. 29. FIG. 32 shows indicator circuitry 550 which includes the inspiration LED indicator 158 which also responds to a power-on indication when the system is first turned on and the low battery LED indicator 160 which are both controlled from the microprocessor 75, and the antenna LED indicator 162 which light in response to a detected disconnect of the RF output antenna.

Figure 33:
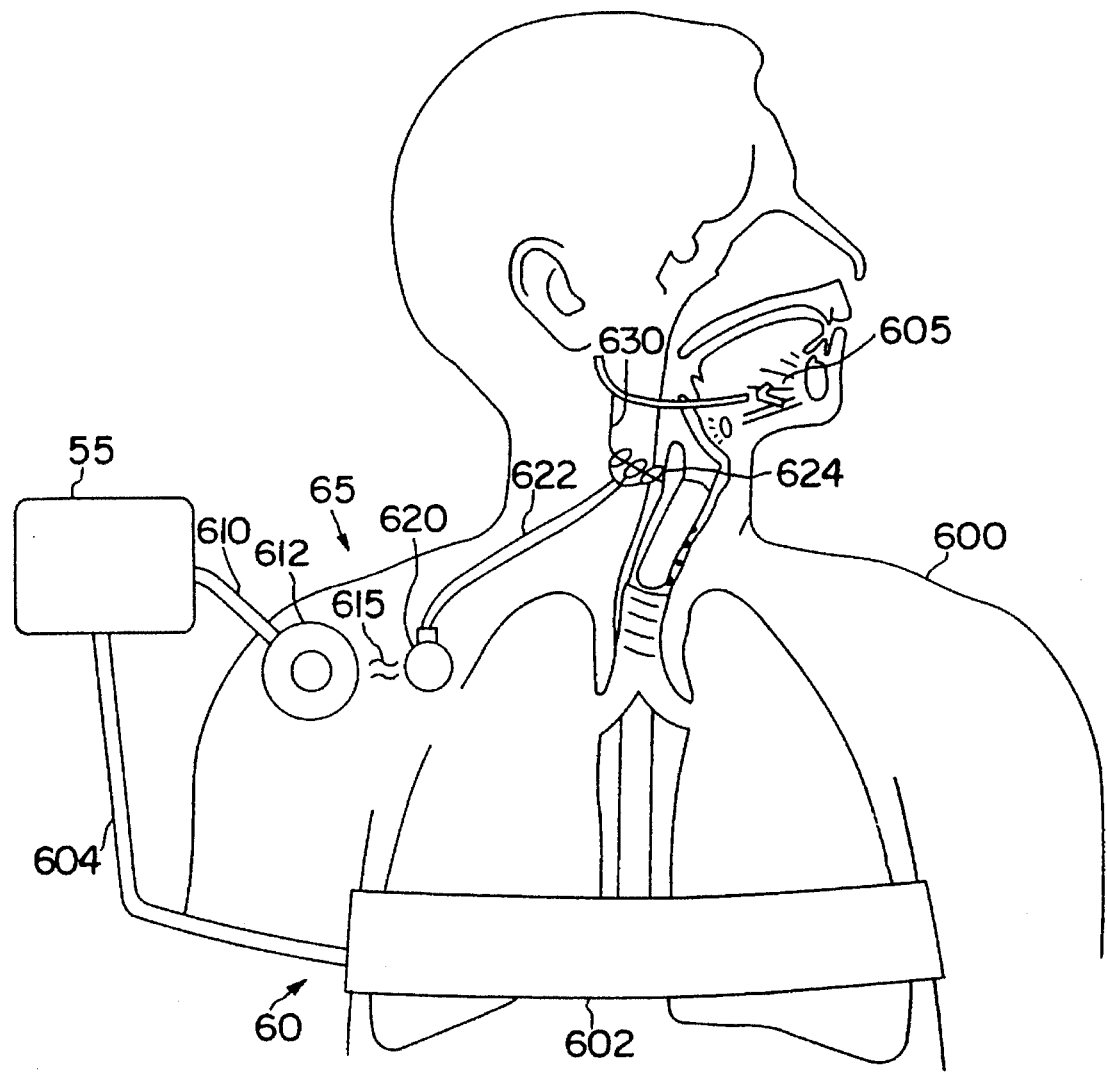
FIG. 33 is a diagram of the apnea treatment device of FIG. 5 as it is applied to a patient.

In FIG. 33, the system as described above is shown as it is used on a patient 600 with an external transmitter/controller 55, a respiratory transducer 60 in the form of a belt 602 around the patient's chest and lead 604 extending from the belt 602 to the transmitter/controller 55 to provide respiratory waveform information to the transmitter/controller 55. In response to the sensed waveform, transmitter/controller 55 sends stimulus pulses through an antenna/electrode system 65 to stimulate an upper airway muscle 610 (i.e. the genioglossus muscle) of the patient 600. The antenna/electrode system 65 is connected to the transmitter/controller 55 by a lead 610 and output antenna 612. The output antenna 612 is coupled by RF signals 615 to a receiving antenna 620 which is connected to a stimulation electrode 624 by a lead 622. The stimulation electrode 624 is positioned to stimulate the hypoglossal nerve 630.

Figure 34:
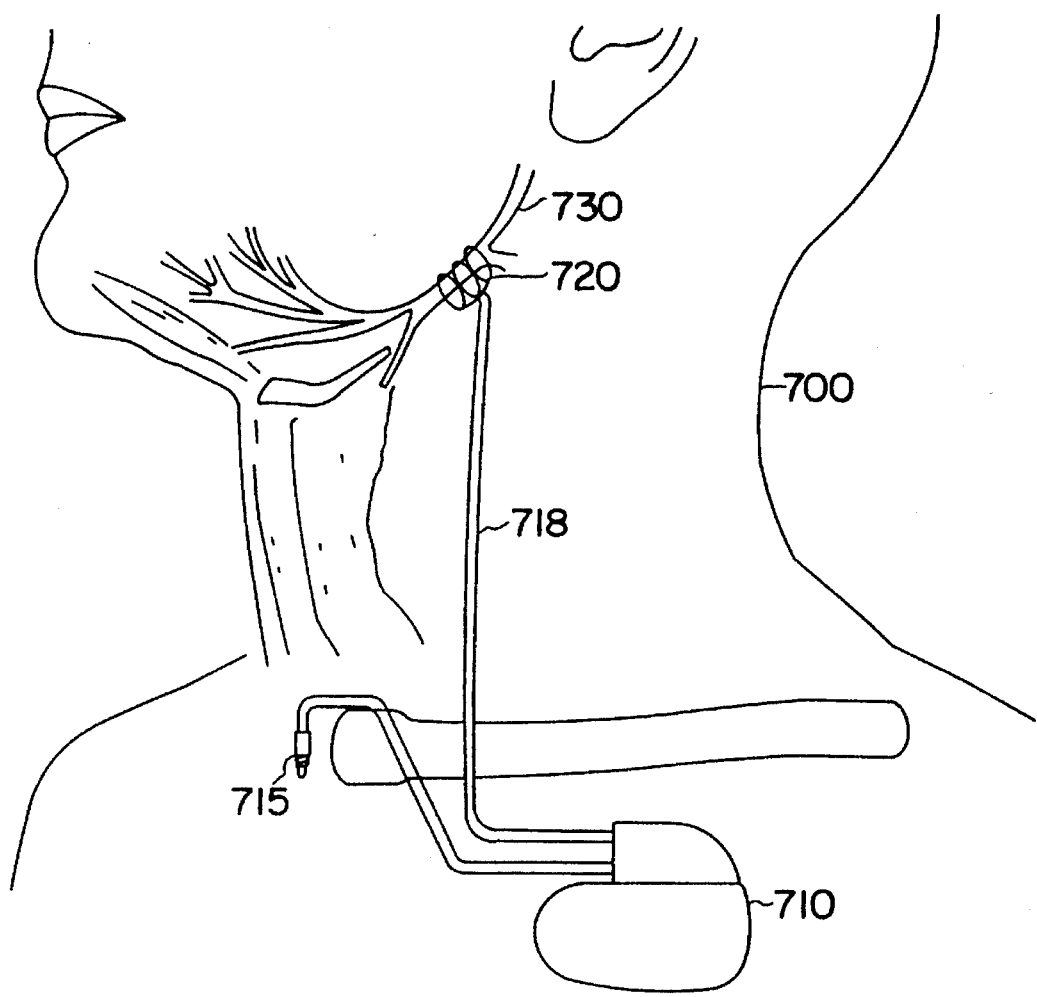
FIG. 34 is an embodiment of the invention using an implanted pulse generator and implanted intrathoracic pressure sensor.

A device substantially as described above can also be implemented in a fully implantable stimulation system such as that shown in FIG. 34. In FIG. 34, an implantable pulse generator 710 (e.g. a Medtronic ITREL II Model 7424 modified to include an input from a respiratory sensor) can be implanted in a patient 700 with respiratory sensing from a pressure sensor 715. The Medtronic ITREL II implantable neurostimulator has advanced programmable features permitting mode changes by transcutaneous RF telemetry. The patient-controllable parameters of the device's operation can therefore be controlled by the patient through a small, handheld telemetry device while the physician can preset additional operational parameters of the device through an external programmer. The pressure sensor 715 is dynamic dp/dt type of pressure sensor such as that disclosed in U.S. Pat. No. 4,407,296 to Anderson or U.S. Pat. No. 4,485,813 issued to Anderson et al which are incorporated herein by reference in their entirety. The pressure sensor 715 is surgically implanted in a structure which has pressure continuity with the intrapleural space such as the suprasternal notch, the space between the trachea and esophagus or an intercostal placement. The suprasternal notch is a well known structure on the upper chest just above the sternum that is an anatomical continuity with the intrapleural space. It is also well known that changes in intrapleural pressure provide a characteristic respiratory waveform that is very similar in form to that produced by the respiratory belt and which could be analyzed in the same manner as set forth above to produce synchronous stimulation. Additional or substitute methods for respiratory effort detection include measurement of thoracic impedance, intracostal EMG, or diaphragm EMG. Inspiration-synchronous stimulation is provided from the pulse generator 710 through a lead 718 to an electrode 720 around the hypoglossal nerve 730.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

I claim:

1. A method for determining the validity of a respiratory effort waveform from a signal having non-respiratory artifacts comprising the steps of:

(a) monitoring a respiratory effort waveform of the patient for at least one time parameter of the waveform characteristic of a non-respiratory artifact; and (b) comparing the parameter value with a predetermined limit having as a lower limit a fixed time period and as an upper limit a time period calculated from a baseline average of the parameter, the valid respiratory waveform indicated by the parameter value being between the upper limit and lower limit.

2. The method of claim 1 wherein the parameter is selected from the group consisting of inspiratory T1 rise time, inspiratory T2 time-to-peak, time of inspiratory T3 onset to expiratory offset, inspiratory peak-to-peak time, expiratory peak-to-peak time and breath-to-breath time.

3. The method of claim 2 wherein the parameter is inspiratory rise time, the lower limit is about 220 milliseconds and the upper limit is a baseline average for the parameter plus an amount in the range of about 625 to 950 milliseconds.

4. The method of claim 2 wherein the parameter is inspiratory time-to-peak, the lower limit is about 750 milliseconds and the upper limit is a baseline average for the parameter plus an amount in the range of about 875 to 1300 milliseconds.

5. The method of claim 2 wherein the parameter is time of inspiratory onset to expiratory offset, the lower limit is about 1000 milliseconds and the upper limit is a baseline average for the parameter plus an amount in the range of about 1125 to 1700 milliseconds.

6. The method of claim 2 wherein the parameter is inspiratory peak-to-peak time, the lower limit is about 2000 milliseconds and the upper limit is a baseline average for the parameter plus an amount in the range of about 2000 to 4000 milliseconds.

7. The method of claim 2 wherein the parameter is expiratory peak-to-peak time, the lower limit is about 2000 milliseconds and the upper limit is a baseline average for the parameter plus an amount in the range of about 2000 to 4000 milliseconds.

8. The method of claim 2 wherein the parameter is breath-to-breath time, the lower limit is about 2000 milliseconds and the upper limit is a baseline average for the parameter plus an amount in the range of about 2000 to 4000 milliseconds.

9. The method of claim 1 also comprising the steps of monitoring multiple parameters of the waveform and comparing the multiple parameters with respective predetermined limits, the valid respiratory waveform determined by the multiple parameter values being within the respective predetermined limits.

10. The method of claim 1 also comprising the step of adjusting the predetermined limit according to the requirements of the patient.

11. An apparatus for determining the validity of a respiratory effort waveform from a signal having non-respiratory artifacts comprising:

(a) monitoring means for monitoring a respiratory effort waveform of the patient for at least one time parameter of the waveform characteristic of a non-respiratory artifact; and (b) comparison means associated with said monitoring means for comparing the parameter value with a predetermined limit having as a lower limit a fixed time period and as an upper limit a time period calculated from a baseline average of the parameter, the valid respiratory waveform indicated by the parameter value being between the upper limit and lower limit.

12. The apparatus of claim 11 wherein the parameter is selected from the group consisting of inspiratory rise time, inspiratory time-to-peak, time of inspiratory onset to expiratory offset, inspiratory peak-to-peak time, expiratory peak-to-peak time and breath-to-breath time.

13. The apparatus of claim 12 wherein the parameter is inspiratory rise time, the lower limit is about 220 milliseconds and the upper limit is a baseline average for the parameter plus an amount in the range of about 625 to 950 milliseconds.

14. The apparatus of claim 12 wherein the parameter is inspiratory time-to-peak, the lower limit is about 750 milliseconds and the upper limit is a baseline average for the parameter plus an amount in the range of about 875 to 1300 milliseconds.

15. The apparatus of claim 12 wherein the parameter is time of inspiratory onset to expiratory offset, the lower limit is about 1000 milliseconds and the upper limit is a baseline average for the parameter plus an amount in the range of about 1125 to 1700 milliseconds.

16. The apparatus of claim 12 wherein the parameter is inspiratory peak-to-peak time, the lower limit is about 2000 milliseconds and the upper limit is a baseline average for the parameter plus an amount in the range of about 2000 to 4000 milliseconds.

17. The apparatus of claim 12 wherein the parameter is expiratory peak-to-peak time, the lower limit is about 2000 milliseconds and the upper limit is a baseline average for the parameter plus an amount in the range of about 2000 to 4000 milliseconds.

18. The apparatus of claim 12 wherein the parameter is breath-to-breath time, the lower limit is about 2000 milliseconds and the upper limit is a baseline average for the parameter plus an amount in the range of about 2000 to 4000 milliseconds.

19. The apparatus of claim 12 also comprising adjusting means associated with said monitoring means and said comparison means for adjusting the predetermined limit according to the requirements of the patient.

20. The apparatus of claim 12 wherein the monitoring means and comparison means include means for monitoring and comparing multiple parameters of the waveform.

* * * * *